(12) United States Patent
Hutchins et al.

(10) Patent No.: US 8,231,621 B2
(45) Date of Patent: Jul. 31, 2012

(54) METHOD OF AND APPARATUS FOR POSITIONING AND MAINTAINING THE POSITION OF ENDOSCOPIC INSTRUMENTS

(75) Inventors: John E. Hutchins, North Attleboro, MA (US); Mark L. Adams, Stoughton, MA (US); Mark Mallaby, Indianapolis, IN (US); Scott E. Swaffar, Bloomington, IN (US); Martin G. Donofrio, Gosport, IN (US); Oscar R. Carrillo, Attleboro, MA (US); Tracy Gandolfi, Hopedale, MA (US); Mike Mangano, Tokyo (JP); Bob Reynolds, Northboro, MA (US); Russell F. Durgin, Attleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 216 days.

(21) Appl. No.: 12/639,709

(22) Filed: Dec. 16, 2009

(65) Prior Publication Data
US 2010/0094087 A1    Apr. 15, 2010

Related U.S. Application Data

(63) Continuation of application No. 10/991,477, filed on Nov. 19, 2004, now Pat. No. 7,635,363, which is a continuation of application No. 10/003,678, filed on Dec. 6, 2001, now Pat. No. 6,827,718, which is a continuation-in-part of application No. 09/928,655, filed on Aug. 14, 2001, now Pat. No. 6,676,659.

(51) Int. Cl.
*A61B 18/18* (2006.01)
*A61B 17/32* (2006.01)
*A61B 17/20* (2006.01)

(52) U.S. Cl. ............... 606/47; 606/167; 604/22
(58) Field of Classification Search .......... 606/39, 606/47, 127, 128, 159, 167, 170; 604/22
See application file for complete search history.

(56) References Cited

U.S. PATENT DOCUMENTS

| | | | |
|---|---|---|---|
| 1,204,053 A | 11/1916 | Moore | |
| 1,539,831 A | 6/1925 | Day | |
| 2,623,520 A | 12/1952 | Bamford, Jr. et al. | |
| 3,015,869 A | 1/1962 | Rapata | |
| 3,108,593 A | 10/1963 | Glassman | |
| 3,536,281 A | 10/1970 | Meehan et al. | |
| 3,955,578 A | 5/1976 | Chamness et al. | |
| 4,228,802 A | 10/1980 | Trott | |
| 4,262,676 A | 4/1981 | Jamshidi | |

(Continued)

FOREIGN PATENT DOCUMENTS
EP    0 388 112 A2    9/1990

(Continued)

*Primary Examiner* — Julian Woo
(74) *Attorney, Agent, or Firm* — Seager, Tufte & Wickhem, LLC

(57) ABSTRACT

The present invention provides an apparatus for, and a method of, accurate positioning of endoscopic instruments. Accurate positioning of the instruments is accomplished through the inclusion of a steering ability within the device. After the endoscopic instrument is properly positioned, the present invention may use rapid exchange technology, soft locks, and mechanical locks to maintain the position of the endoscopic instrument. Rapid exchange technology is used to minimize displacement forces present on the guidewire or catheters. Soft locks and mechanical locks resist movements caused by displacement forces.

17 Claims, 35 Drawing Sheets

U.S. PATENT DOCUMENTS

| | | | |
|---|---|---|---|
| 4,345,606 A | 8/1982 | Littleford |
| RE31,855 E | 3/1985 | Osborne |
| 4,627,837 A | 12/1986 | Gonzalo |
| 4,696,668 A | 9/1987 | Wilcox |
| 4,705,041 A | 11/1987 | Kim |
| 4,748,982 A | 6/1988 | Horzewski et al. |
| 4,762,129 A | 8/1988 | Bonzel |
| 4,771,777 A | 9/1988 | Horzewski et al. |
| 4,781,677 A | 11/1988 | Wilcox |
| 4,835,824 A | 6/1989 | Durham et al. |
| 4,844,092 A | 7/1989 | Rydell et al. |
| 4,900,184 A | 2/1990 | Cleveland |
| 4,905,667 A | 3/1990 | Foerster et al. |
| 4,917,103 A | 4/1990 | Gambale et al. |
| 4,927,418 A | 5/1990 | Dake et al. |
| 4,928,693 A | 5/1990 | Goodin et al. |
| 4,932,413 A | 6/1990 | Shockey et al. |
| 4,946,443 A | 8/1990 | Hauser et al. |
| 4,988,356 A | 1/1991 | Crittenden et al. |
| 4,997,421 A | 3/1991 | Palsrok et al. |
| 5,024,617 A | 6/1991 | Karpiel |
| 4,762,129 A | 7/1991 | Bonzel |
| 5,035,696 A | 7/1991 | Rydell |
| 5,040,548 A | 8/1991 | Yock |
| 5,061,273 A | 10/1991 | Yock |
| 5,064,414 A | 11/1991 | Revane |
| 5,066,295 A | 11/1991 | Kozak et al. |
| 5,084,054 A | 1/1992 | Bencini et al. |
| 5,125,915 A | 6/1992 | Berry et al. |
| 5,135,535 A | 8/1992 | Kramer |
| 5,147,377 A | 9/1992 | Sahota |
| 5,152,772 A | 10/1992 | Sewell, Jr. |
| 5,158,545 A | 10/1992 | Trudell et al. |
| 5,163,942 A | 11/1992 | Rydell |
| 5,167,634 A | 12/1992 | Corrigan, Jr. et al. |
| 5,176,702 A | 1/1993 | Bales et al. |
| 5,195,978 A | 3/1993 | Schiffer |
| 5,201,732 A | 4/1993 | Parins et al. |
| 5,205,822 A | 4/1993 | Johnson et al. |
| 5,232,445 A | 8/1993 | Bonzel |
| 5,250,033 A | 10/1993 | Evans et al. |
| 5,279,562 A | 1/1994 | Sirhan et al. |
| 5,282,479 A | 2/1994 | Havran |
| 5,290,232 A | 3/1994 | Johnson et al. |
| 5,290,241 A | 3/1994 | Kraus et al. |
| 5,300,085 A | 4/1994 | Yock |
| 5,306,247 A | 4/1994 | Pfenninger |
| 5,308,318 A | 5/1994 | Plassche, Jr. |
| 5,312,338 A | 5/1994 | Nelson et al. |
| 5,320,602 A | 6/1994 | Karpiel |
| 5,324,259 A | 6/1994 | Taylor et al. |
| 5,324,269 A | 6/1994 | Miraki |
| 5,325,746 A | 7/1994 | Anderson |
| 5,327,905 A | 7/1994 | Avitall |
| 5,328,472 A | 7/1994 | Steinke et al. |
| 5,334,143 A | 8/1994 | Carroll |
| 5,334,187 A | 8/1994 | Fischell et al. |
| 5,342,292 A | 8/1994 | Nita et al. |
| 5,350,395 A | 9/1994 | Yock |
| 5,364,355 A | 11/1994 | Alden et al. |
| 5,364,376 A | 11/1994 | Horzewski et al. |
| 5,370,623 A | 12/1994 | Kreamer |
| 5,382,536 A | 1/1995 | Malhi et al. |
| 5,389,087 A | 2/1995 | Miraki |
| 5,397,302 A | 3/1995 | Weaver et al. |
| 5,423,844 A | 6/1995 | Miller |
| 5,439,006 A | 8/1995 | Brennen et al. |
| 5,451,233 A | 9/1995 | Yock |
| 5,454,790 A | 10/1995 | Dubrul |
| 5,458,584 A | 10/1995 | Ginn et al. |
| 5,458,605 A | 10/1995 | Klemm |
| 5,480,389 A | 1/1996 | McWha et al. |
| 5,490,837 A | 2/1996 | Blaeser et al. |
| 5,496,346 A | 3/1996 | Horzewski et al. |
| 5,501,227 A | 3/1996 | Yock |
| 5,531,700 A | 7/1996 | Moore et al. |
| 5,536,248 A | 7/1996 | Weaver et al. |
| 5,540,236 A | 7/1996 | Ginn |
| 5,547,469 A | 8/1996 | Rowland et al. |
| 5,549,367 A | 8/1996 | Matsuto |
| 5,573,530 A | 11/1996 | Fleury et al. |
| 5,599,299 A | 2/1997 | Weaver et al. |
| 5,599,300 A | 2/1997 | Weaver et al. |
| 5,609,601 A | 3/1997 | Kolesa et al. |
| 5,613,949 A | 3/1997 | Miraki |
| 5,626,600 A | 5/1997 | Horzewski et al. |
| 5,662,647 A | 9/1997 | Crow et al. |
| 5,683,362 A | 11/1997 | Rowland et al. |
| 5,706,827 A | 1/1998 | Ehr et al. |
| 5,707,363 A | 1/1998 | Crawford et al. |
| 5,725,504 A | 3/1998 | Collins |
| 5,788,681 A | 8/1998 | Weaver et al. |
| 5,801,416 A | 9/1998 | Choi et al. |
| 5,810,807 A | 9/1998 | Ganz et al. |
| 5,833,706 A | 11/1998 | St. Germain et al. |
| 5,843,028 A | 12/1998 | Weaver et al. |
| 5,849,016 A | 12/1998 | Suhr |
| 5,868,698 A | 2/1999 | Rowland et al. |
| 5,879,333 A | 3/1999 | Smith |
| 5,921,971 A | 7/1999 | Agro et al. |
| 5,957,882 A | 9/1999 | Nita et al. |
| 5,971,994 A | 10/1999 | Fritzsch |
| 5,978,699 A | 11/1999 | Fehse et al. |
| 5,984,920 A | 11/1999 | Steinbach |
| 6,001,114 A | 12/1999 | Ouchi |
| 6,007,522 A | 12/1999 | Agro et al. |
| 6,010,464 A | 1/2000 | Galdonik et al. |
| 6,015,381 A | 1/2000 | Ouchi |
| 6,048,346 A | 4/2000 | Reiley et al. |
| 6,096,009 A | 8/2000 | Windheuser et al. |
| 6,152,910 A | 11/2000 | Agro et al. |
| 6,235,026 B1 | 5/2001 | Smith |
| 6,533,782 B2 * | 3/2003 | Howell et al. ............ 606/47 |
| 6,746,442 B2 | 6/2004 | Agro et al. |
| 6,827,718 B2 | 12/2004 | Hutchins et al. |

FOREIGN PATENT DOCUMENTS

| | | |
|---|---|---|
| EP | 0 792 657 A2 | 9/1997 |
| EP | 0 801 955 | 10/1997 |
| JP | 61-265137 A | 11/1986 |
| JP | 10-500336 A | 1/1998 |
| JP | 2001-514922 A | 9/2001 |
| JP | 2004-527267 A | 9/2004 |
| WO | 92/03963 A1 | 3/1992 |
| WO | 95/31246 A1 | 11/1995 |
| WO | 96/33764 A1 | 10/1996 |
| WO | 98/10820 A1 | 3/1998 |
| WO | 98/10821 A1 | 3/1998 |
| WO | 99/08616 A1 | 2/1999 |
| WO | 99/59664 A1 | 11/1999 |
| WO | 00/33724 A2 | 6/2000 |
| WO | 00/42926 A1 | 7/2000 |
| WO | 00/69499 A1 | 11/2000 |
| WO | 00/69500 A1 | 11/2000 |
| WO | 00/71197 A1 | 11/2000 |
| WO | 02/13711 A9 | 2/2002 |

* cited by examiner

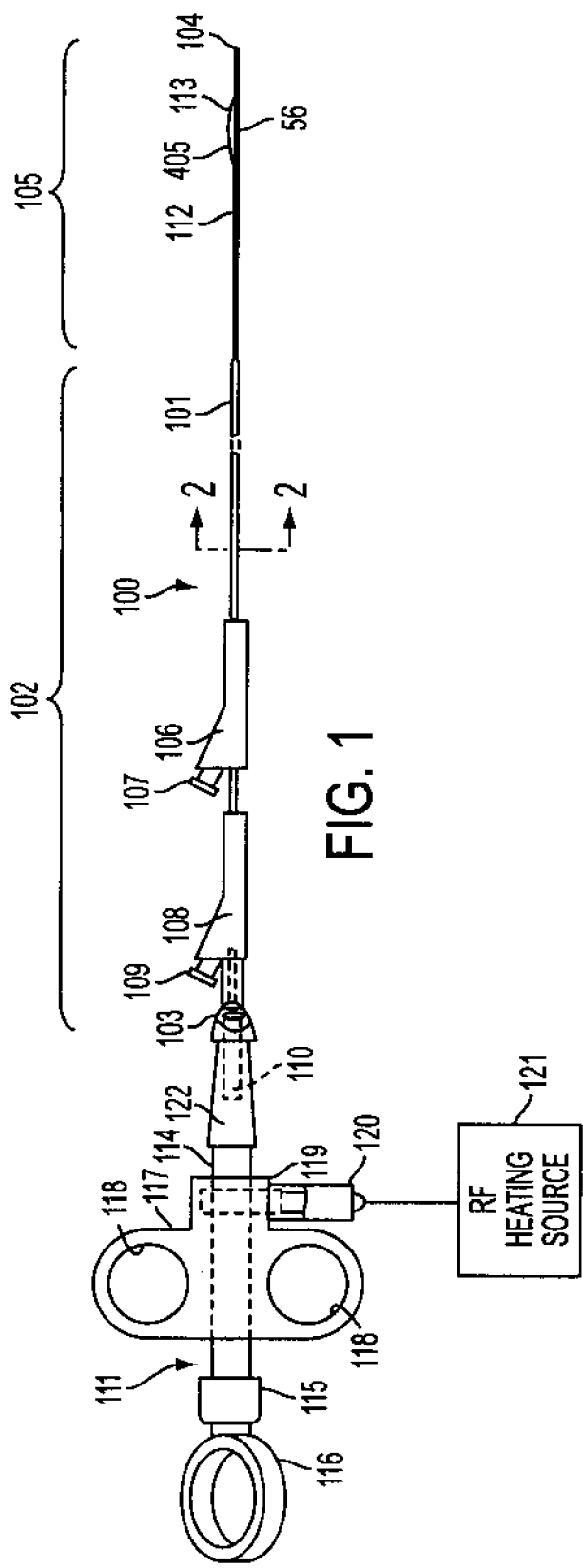
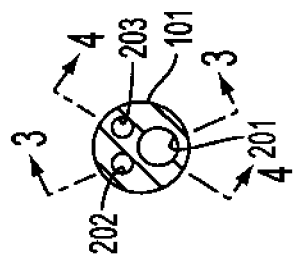

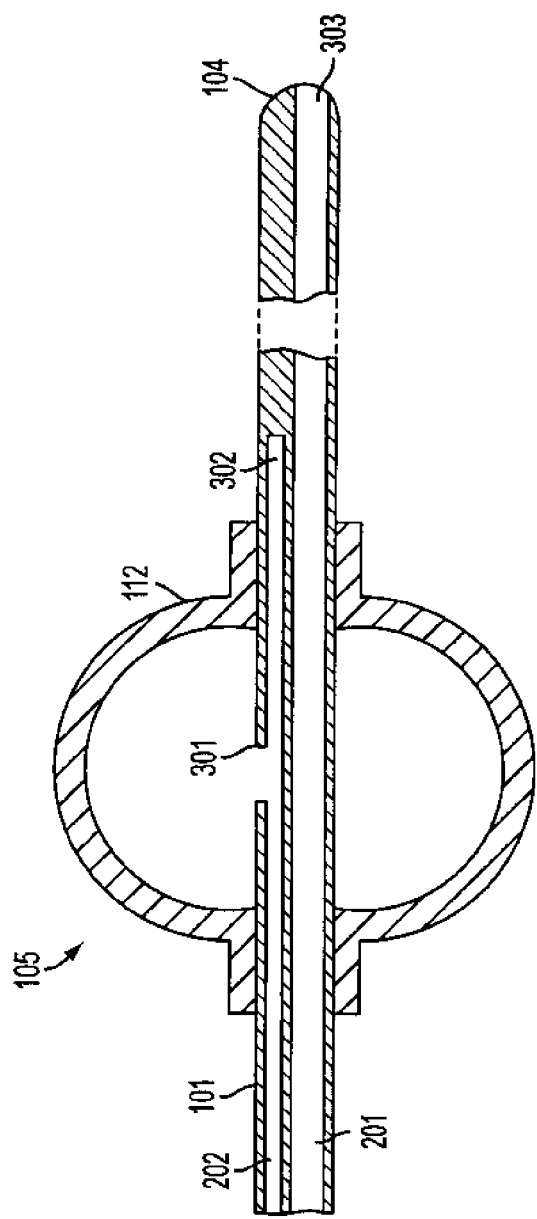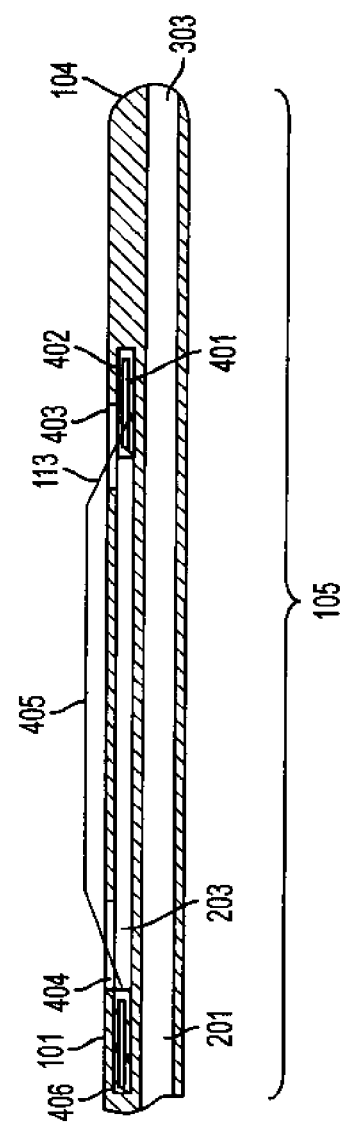

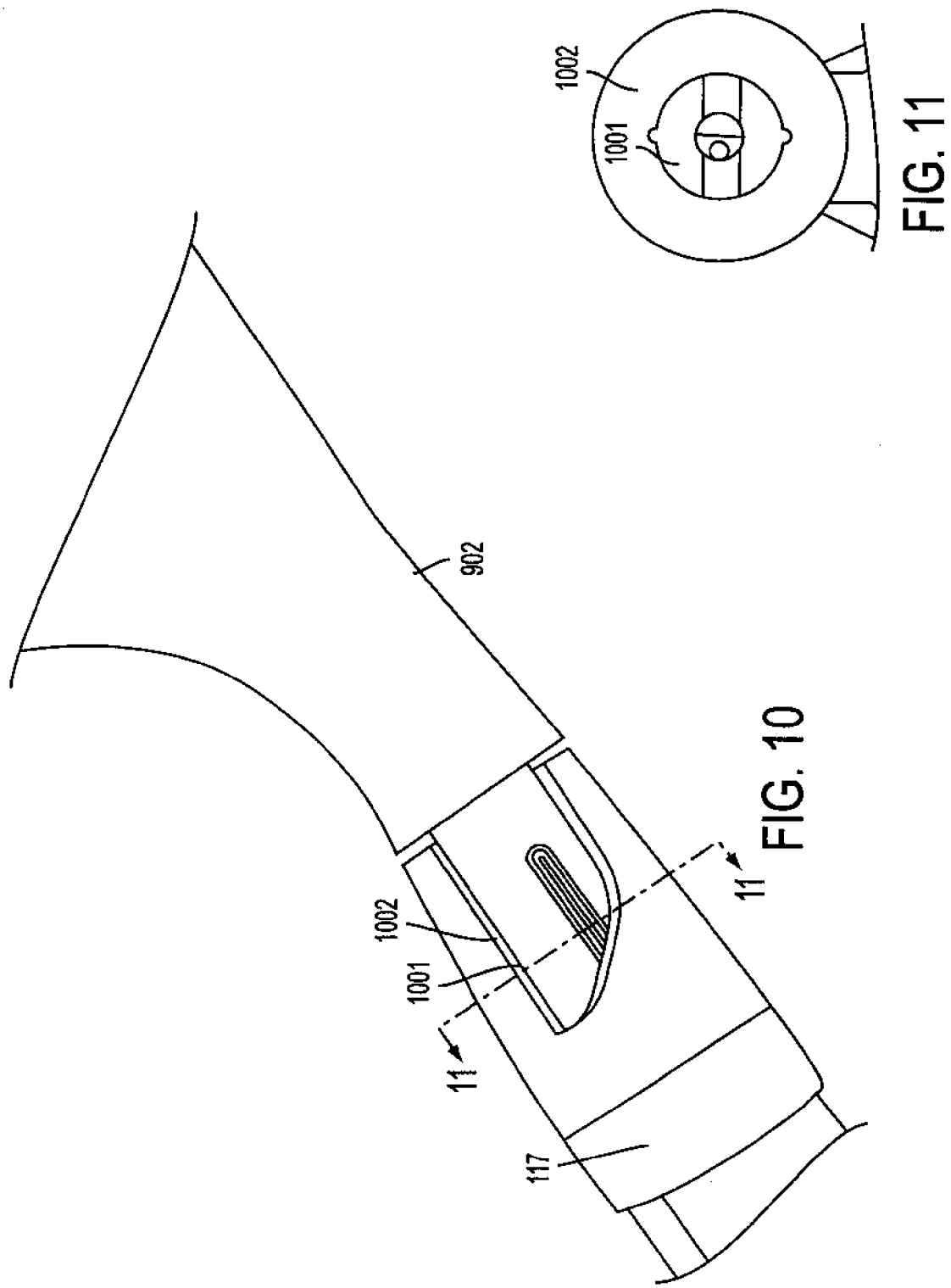

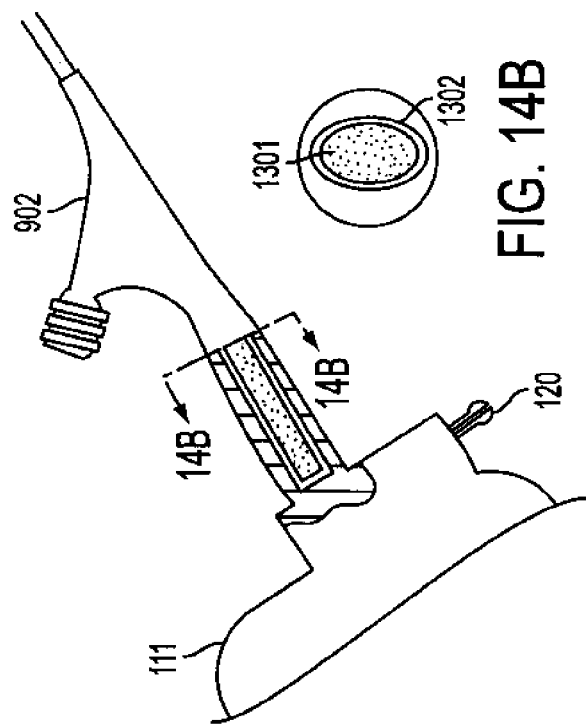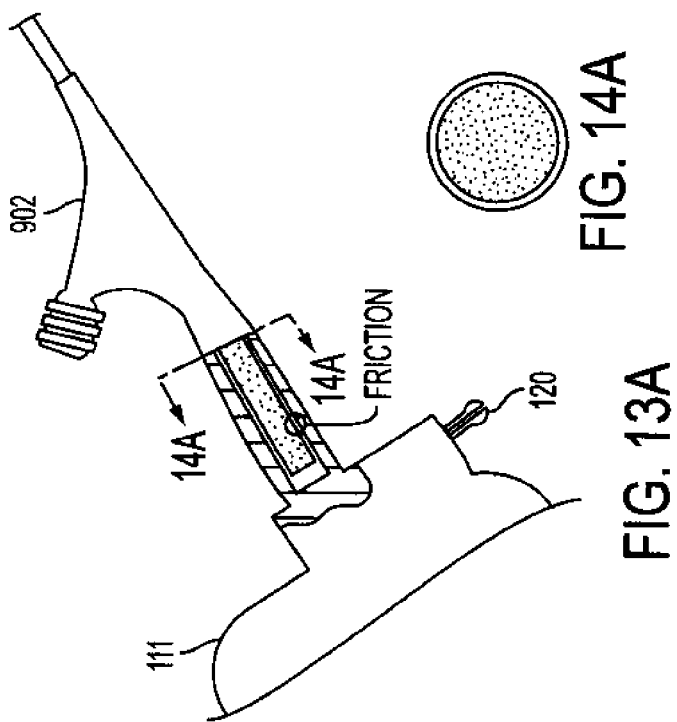

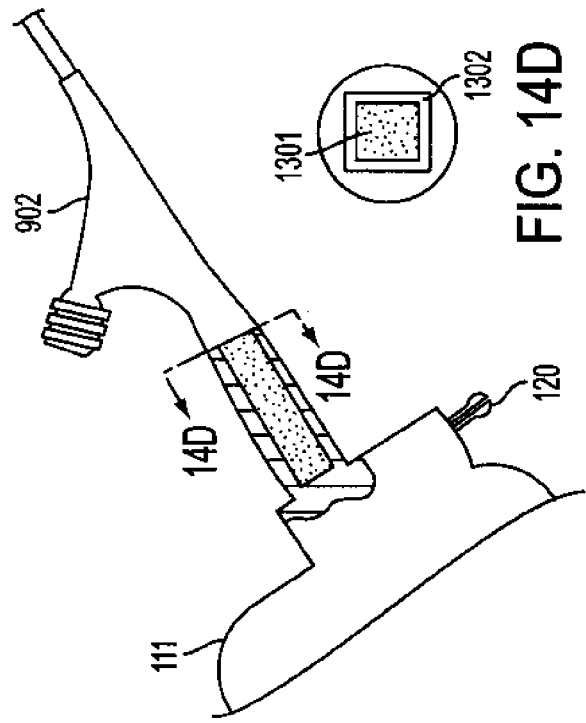
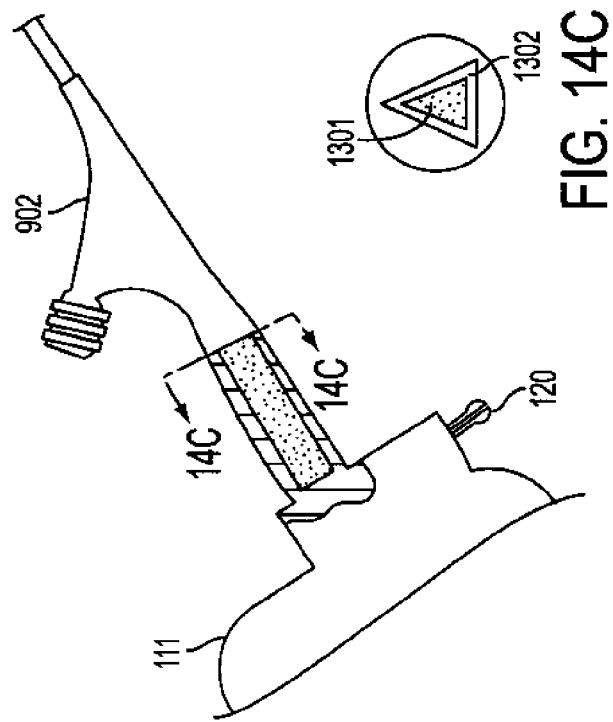

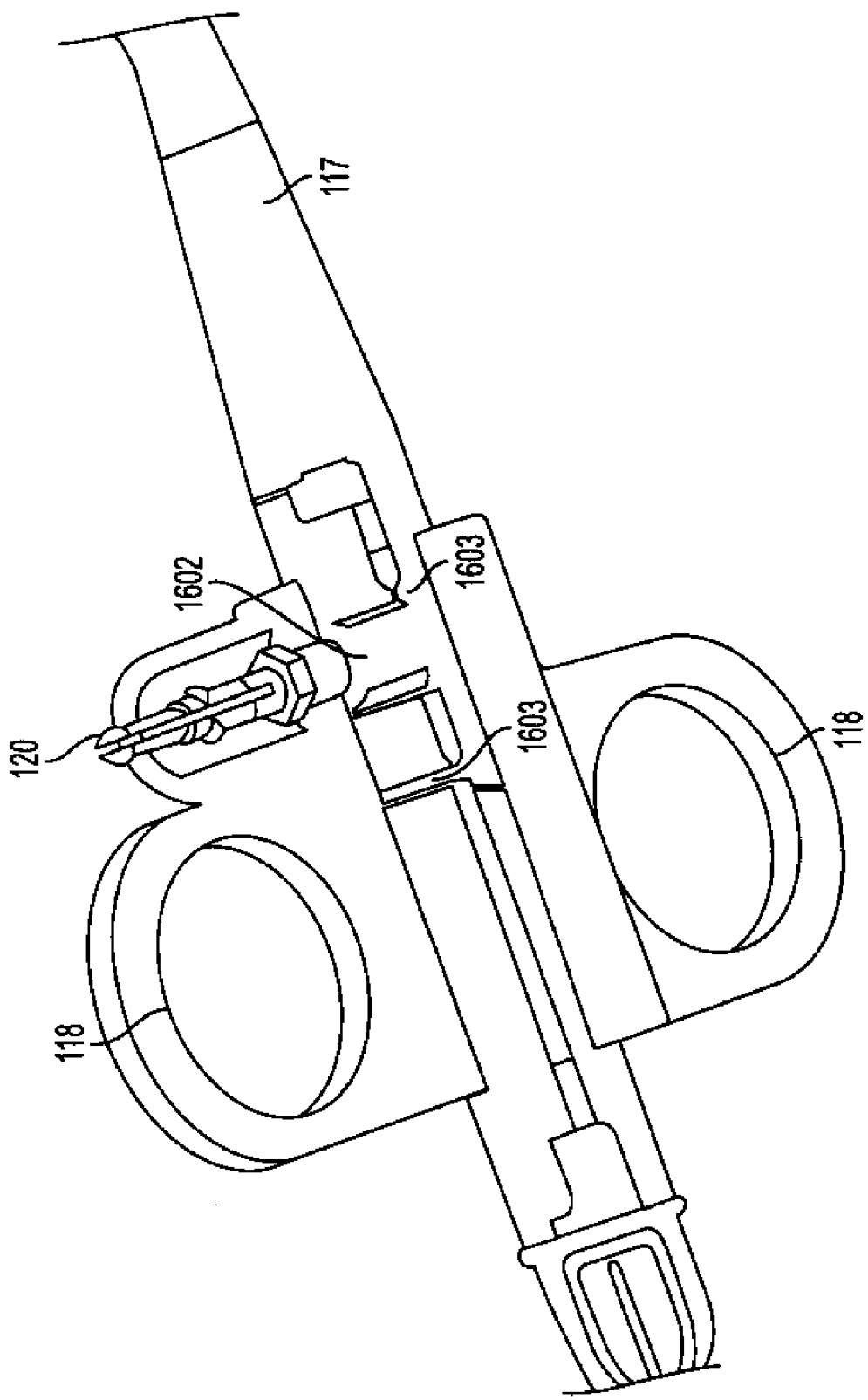

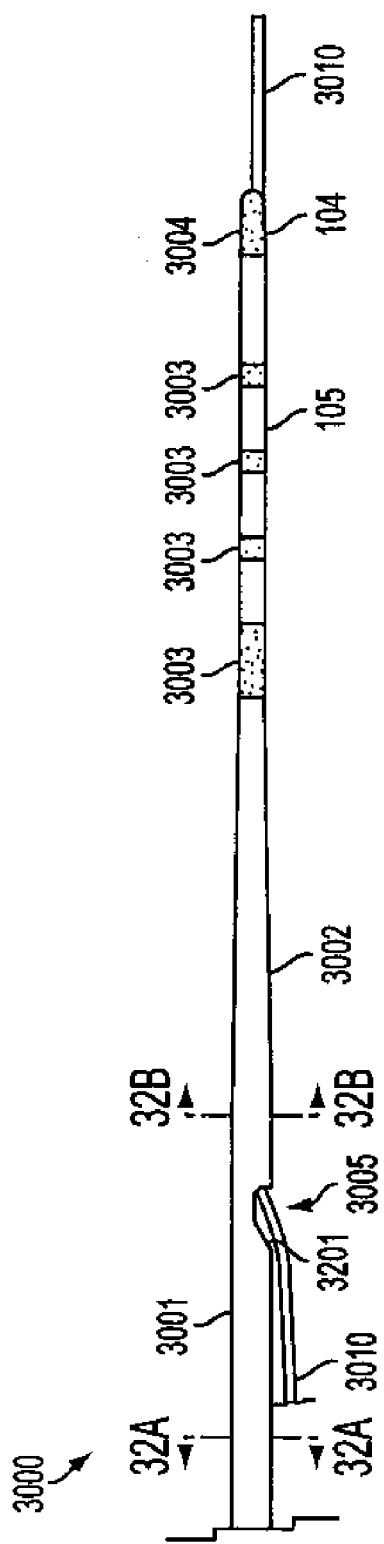
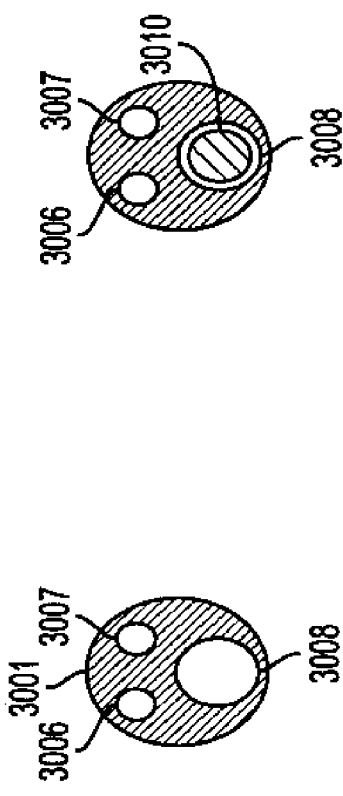
FIG. 32
FIG. 32A
FIG. 32B

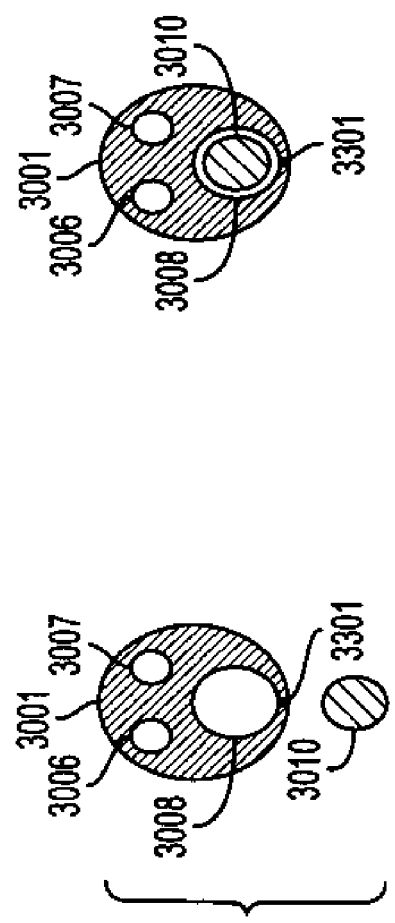
FIG. 33
FIG. 33A
FIG. 33B

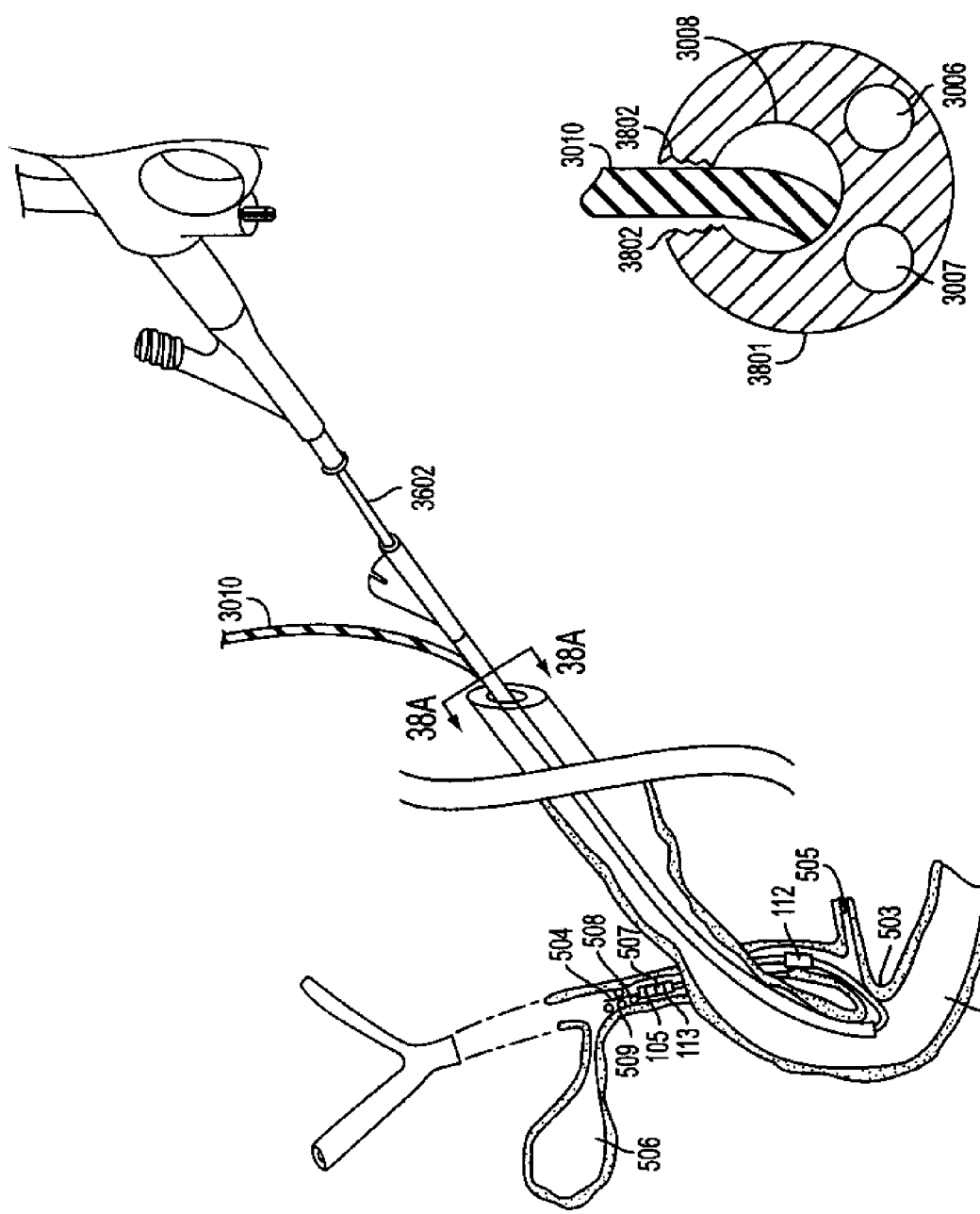

METHOD OF AND APPARATUS FOR POSITIONING AND MAINTAINING THE POSITION OF ENDOSCOPIC INSTRUMENTS

RELATED APPLICATIONS

This application is a continuation of U.S. patent application Ser. No. 10/991,477, filed Nov. 19, 2004, now U.S. Pat. No. 7,635,363, which is a continuation of U.S. patent application Ser. No. 10/003,678, filed Dec. 6, 2001, now U.S. Pat. No. 6,827,718, which is a continuation-in-part U.S. patent application Ser. No. 09/928,655, filed Aug. 14, 2001, now U.S. Pat. No. 6,676,659, the entire disclosures of which are all incorporated herein by reference in their entirety.

This application is also related to commonly assigned U.S. Pat. Nos. 5,921,971; 6,007,522; 6,096,009; 5,547,469; 5,683,362; and 5,868,698, the entire disclosures of which are all incorporated herein by reference in their entirety.

BACKGROUND

1. Field of the Invention

The present invention relates to apparatus and methods used in positioning and maintaining the position of devices used in catheter procedures within the human anatomy. The present invention includes steerable devices, locking mechanisms and rapid exchange technologies to minimize or eliminate movement of endoscopic instruments during endoscopic procedures.

2. Description of Related Art

Historically, the migration of gallstones into an individual's common bile duct was corrected by general surgical procedures. A surgeon would incise the bile duct and remove the gallstones and normally remove the gallbladder. In recent years, less invasive treatment modalities have replaced these general surgical procedures and reduced patient trauma, long hospital stays and recovery periods.

For example, U.S. Pat. No. 4,696,668 and U.S. Pat. No. 4,781,677, both to Wilcox, disclose a treatment modality involving the administration of a dissolution agent in the bile duct to essentially dissolve any gallstones. More specifically, a catheter contains several lumens for inflating and deflating each of two balloons, venting bile, and infusing and aspirating the dissolution agent. Inflating the balloons occludes the bile duct at two spaced sites and creates a sealed spaced that receives the dissolution agent. As the space is sealed from the remaining biliary tree, the dissolution agent finds access to the gallbladder and any gallstones therein through the cystic duct with the exclusion of bile from the gallbladder fundus. The dissolution agent also will be confined in high concentration around bile duct gallstones. After the gallstones dissolve, the balloons are deflated, and the catheter can be withdrawn. In this particular approach, the catheter is directed into the biliary tree using a standard duodenoscope that passes through the alimentary tract. Although this and analogous approaches have the potential of minimizing patient trauma, such treatments require extended placement of the duodenoscope in the patient, exhibit low efficacy and introduce a potential for adverse reactions to the dissolution agents.

In an alternative approach, a surgeon directs a surgical extractor into the biliary tree through at least an incision in the bile duct. For example, in U.S. Pat. No. 3,108,593 to Glassman a surgeon incises both the bile duct and duodenum. Then the surgeon directs an extractor through the bile duct incision, biliary tree, sphincter of Oddi and duodenum to exit through the duodenum incision. This extractor includes a series of longitudinally spaced cages for trapping any gallstones in the bile duct and removing them through either of the incisions.

U.S. Pat. No. 4,627,837 to Gonzalo discloses a catheter device with a pair of inflatable balloons at its distal end. This catheter is led through an incision in the bile duct toward the duodenum. After the distal balloon passes through the sphincter of Oddi, both balloons are expanded to anchor the catheter in place. This enables the catheter to be used for irrigating and flushing through other lumens in order to capture any gallstone in the second balloon for removal through the incised bile duct.

In accordance with still another modality as for the treatment of strictures, a surgeon may insert a catheter device through the bile duct or duodenum for the purpose of dilating or enlarging the sphincter of Oddi. For example, U.S. Pat. No. 4,705,041 to Kim discloses a dilator that is directed through an incision in the bile duct and the sphincter of Oddi. An expandable tip dilates the sphincter of Oddi. U.S. Pat. No. 5,035,696 to Rydell discloses an electrosurgical instrument that is directed through the duodenum and to the sphincter of Oddi for performing a sphincterotomy. This apparatus contains a cutting wire that is heated to cut the sphincter muscle. U.S. Pat. No. 5,024,617 to Karpiel discloses a similar device that can be directed through a duodenoscope. U.S. Pat. No. 5,152,772 to Sewell, Jr. discloses a device for performing a sphincterotomy that is directed through an incision in the bile duct and includes a knife for cutting the sphincter muscle.

The use of the duodenoscope and sphincterotomy devices, such as shown in the Rydell and Karpiel patents, enables an internist to diagnose and treat problems in the biliary tree with less patient invasion than previously possible. For example, modalities as described in these patents eliminate the surgery needed for incising the bile duct. Consequently, these modalities can be performed as outpatient or day surgical procedures. These procedures greatly reduce patient trauma, the length of a hospital stay and recovery times.

The reduced patient trauma, hospital stays and recovery times has resulted in a growth in the number of endoscopic procedures performed for treating abnormal pathologies within the alimentary canal system and biliary tree (including the biliary, hepatic, and pancreatic ducts). The endoscope provides access to the general area of a desired duct using direct visualization. However, the duct itself must be navigated using a catheter in conjunction with fluoroscopy and guide wires, Catheters are known for treatment of targeted anatomical regions. Known methods and devices for using biliary catheters for accessing the biliary tree for performing catheter procedures are disclosed in Weaver et al., U.S. Pat. No. 5,397,302 and Karpiel, U.S. Pat. No. 5,320,602, the disclosures of which are herein incorporated by reference. In general, for treatment of an abnormal pathology within a patient's biliary tree, an endoscope is first introduced into the mouth of the patient. The endoscope includes a proximal end and a distal end, and has a lumen extending longitudinally between the proximal and distal ends. The endoscope is guided through the patient's alimentary tract or canal until an opening at the distal end of the endoscope is proximate the area to receive treatment. At this point, the endoscope allows other components, such as a catheter, to access the targeted area.

For visualization or treatment within the biliary tree, the distal end of the endoscope is positioned proximate the papilla of Vater leading to the common bile duct and the pancreatic duct. A catheter is guided through the lumen of the endoscope until a distal tip of the catheter emerges from the opening at the distal end of the endoscope.

The catheter may be used for accessing the biliary tree. The distal end of the catheter is guided through the orifice to the papilla of Vater (located near the sphincter of Oddi) leading to the common bile duct and the pancreatic duct. A guide wire may be used in conjunction with the catheter to facilitate accessing a desired location within the biliary tree. The guide wire is inserted in an opening at a proximal end of the catheter and guided through the catheter until it emerges from the distal end of the catheter.

If visualization of the common bile duct is desired, the guide wire is guided into the common bile duct. The catheter is advanced over the guide wire until the distal end of the catheter is positioned in the common bile duct at the desired location. The catheter is now in position for delivery of contrast media for fluoroscopic visualization of anatomical detail within the common bile duct.

Visualization may reveal selected areas within the common bile duct that require treatment. To treat the selected areas, a different catheter is typically required, necessitating a catheter exchange. A catheter exchange typically involves removing the first catheter from the endoscope over the guide wire, and advancing a second catheter over the guide wire to the desired treatment site. Thus, once the guide wire is in place relative to the targeted area, it is highly desirable to maintain the position of the guide wire during subsequent catheter procedures, including during a catheter exchange procedure. If the guide wire moves during such a procedure, the guide wire may have to be re-directed through the body ducts to the target site, which is often a difficult, time consuming and tedious task.

In addition to performing a catheter exchange procedure, it may also be desirable to perform a guide wire exchange procedure. This may be desirable when, for example, a first guide wire is too large to fit through a desired body duct, or otherwise lacks the desired characteristics. Under these circumstances, a physician may leave the catheter in place, withdraw the first guide wire from the catheter, and insert a second guide wire through the catheter to the desired site. During this procedure, the catheter guides the guide wire to the desired site. Thus, once the catheter is positioned at a target site, it is highly desirable to maintain the position of the catheter during a guide wire exchange procedure so that the second guide wire may be guided directly to the desired site in a minimum amount of time.

For example, if an internist determines that gallstones are present in the biliary tree, particularly the common bile duct, the internist can insert a duodenoscope into the duodenum to view the sphincter of Oddi. Then a first catheter can be advanced through the working channel of the duodenoscope with or without a guidewire and directed through the sphincter of Oddi into the biliary tree. Contrast agent injected through the catheter enables fluoroscopy or other imaging procedures to confirm the presence of gallstones within the biliary tree. Next, the internist exchanges the first catheter for a second catheter for performing a sphincterotomy such as the types disclosed in the above-identified Rydell and Karpiel patents. The second catheter is then exchanged for a third catheter such as shown in the Glassman patent or some other equivalent retrieval catheter for drawings gallstones through the enlarged sphincter of Oddi. Thereafter, the retrieval catheter is manipulated to release the gallstone into the duodenum. The catheter, any guidewire and the duodenoscope can then be removed to complete the procedure.

This procedure is significantly less traumatic to the patient than other prior art procedures because the only incision occurs during the sphincterotomy. However, this procedure, as described above, requires three separate catheters and two catheter exchanges. These exchanges are required because the first, second and third catheters function solely to inject contrast agent to perform the sphincterotomy and to dislodge gallstones, respectively. The time required for performing each catheter exchange can increase patient trauma and increase the duration of the procedure and reduce efficiency. Moreover, each such procedure requires the use of two or three separate catheter devices.

Multi-lumen catheters are available which typically reduce the number of catheters and catheter exchanges used during a procedure and thereby reduce both the time required and the patient's trauma while increasing efficiency. A common problem today concerns the accurate placement of an endoscopic instrument such as a cutting device. Secondly, once the cutting device, such as a sphincterotome, Ultratome, Rapid Exchange, Fluorotome, Papillotome or similar device is properly positioned, the position of the device must be maintained during the cutting procedure. An example of a common problem with these devices is that after the device is positioned and left unattended "set relaxation" occurs in which the bow of a cutting instrument undesirably relaxes or straightens out without operator interaction.

Even with multi-lumen catheters, exchanges may be required. To maintain the position of a guide wire and/or catheter during an exchange, a physician typically must grasp the proximal end of the guide wire and/or catheter with one hand, and perform the corresponding exchange with the other. This is difficult, and often results in the movement of the guide wire and/or catheter.

In general, a need exists for an apparatus and method for accurate positioning of endoscopic instruments, such as cutting devices, and the maintenance of the position of the device.

SUMMARY

Therefore, this invention provides an apparatus for, and a method of, accurate positioning of endoscopic instruments. Accurate positioning of the instruments is accomplished through the inclusion of a steering ability within the device. After the endoscopic instrument is properly positioned, the present invention uses rapid exchange technology, soft locks, and mechanical locks to maintain the position of the endoscopic instrument. Rapid exchange technology is used to minimize displacement forces present on the guidewire or catheters. Soft locks and mechanical locks resist movements caused by displacement forces.

The present invention includes an apparatus for use in a treatment modality including an enlargement procedure to be performed within a patient. In this embodiment the apparatus includes a catheter for being directed through internal passageways in the patient, and the catheter has a proximal end and a distal end. A proximal portion is adjacent to the proximal end and a distal portion is adjacent to the distal end. The catheter includes a first and at least a second generally parallel lumen, which extend between the proximal and the distal portions. The present invention includes a cutting wire for performing the enlargement procedure extending through the second lumen for operating at the distal portion in response to manipulations at the proximal end. The cutting wire has a distal end attached to the catheter at the distal end of the second lumen. A portion of the cutting wire is external to the catheter along a length coextensive with a portion of the distal portion of the catheter. The catheter also includes a handle for operating the cutting wire from a point proximal of the catheter. A rotatable coupling attaches the handle to the catheter and allows the handle to rotate relative to the proximal end of the catheter while engaging and rotating a proximal end of the cutting wire. The rotation of the handle causes the distal portion of the catheter to rotate. The present invention also includes a locking mechanism for locking an orientation of a distal portion of the cutting wire.

This embodiment of the present invention may further include a rotation lock which inhibits further rotation of the handle relative to the proximal end of the catheter and a rotation indicator configured to indicate an amount of rotation of the handle relative to the proximal end of the catheter. The rotation indicator may include a visual indicator of the amount of rotation and the visual indicator may include an index marking and a corresponding scale marking providing an indication of the amount of rotation. The rotation indicator may also include a device providing an audible indication in response to the rotation of the handle relative to the proximal end of the catheter. The locking mechanism of the present invention may include an insert positioned between moving parts of the apparatus to resist movement between the moving parts, or an insert which a guidewire passes through the insert and the insert resists movement of the guidewire. The locking mechanism may include evenly spaced detents in a handle body which interact with one or more pawls located in an active cord insert to resist movement of the active cord insert with respect to the handle body.

In another embodiment of the present invention, the invention includes a method of cutting tissue in a body passage including selecting a catheter having a first lumen configured for receiving a wire guide and a second lumen configured for receiving an electrosurgical cutting wire. The catheter is positioned in the passage at a desired position using an endoscope, and the electrosurgical cutting wire is actuated in the second lumen. In this embodiment, the invention includes orientating the electrosurgical cutting wire by rotating a handle relative to a proximal end of the catheter and fixing an orientation of the electrosurgical cutting wire. The orientation of the electrosurgical cutting wire may be fixed by an insert which creates friction between moving parts in the catheter which resists movement between the moving parts. The orientation may also be fixed with detents which interact with pawls to resist movement between an active cord insert and a handle.

Another embodiment of the present invention includes a catheter handle comprising a rotatable coupling configured to allow free rotation of a proximal end of a catheter and a clamping member configured to engage a proximal end of a device extending through a lumen formed in the catheter, whereby rotation of the handle causes rotation of a proximal end of the device in the lumen and a locking mechanism configured to resist movement in a distal end of the device. In this embodiment, the device may include a cutting wire extending from the proximal end of the catheter to and connecting to a distal end of the catheter. A rotation lock may also be included which is engageable to inhibit a rotation of the handle with respect to the proximal end of the catheter.

Another embodiment of the present invention includes a catheter including a shaft having a proximal end and a distal end. The catheter includes a guidewire lumen carried by the shaft extending from a location proximal the distal end of the shaft to a location proximate the distal end of the shaft. Also included is a cutting device extending from the proximal end of the catheter to a distal portion of the catheter and where a distal portion of the cutting device is exterior to the catheter. In this embodiment, means for accessing the guidewire lumen from a location exterior to the catheter shaft, located distal the proximal end of the shaft, are included. These means include a first opening through the wall of the catheter shaft into the guidewire lumen located proximal the distal end of the shaft and a second opening through the wall of the shaft located proximal the first opening. Also included is a channel which gives access to the guide wire lumen extending longitudinally between the first opening and the second opening. Additionally, means for locking an orientation of the cutting device are also included. In this embodiment, the guidewire lumen may be formed integral to the shaft. Additionally, the channel may include an opening extending longitudinally between the first opening and the second opening in communication with the guidewire lumen. The locking means may include an insert positioned between moving parts used to actuate the cutting device wherein the insert resists movement between the moving parts. The locking means may also include detents located in a handle of the catheter and at least one pawl located on an active cord insert where the active cord insert moves with respect to the handle and the detents cooperate with the pawl to resist movement of the active cord insert.

Another embodiment of the present invention includes a method of positioning a cutting device including a shaft having a proximal end and a distal end, within a patient's lumen comprising the steps of: providing a guidewire lumen within the catheter, extending from a location proximal the distal end of the shaft to a location proximate the distal end of the shaft and providing a port through a sidewall of the shaft into the guidewire lumen, the port located distal of the proximal end of the shaft. In this embodiment, a guidewire is moved through the port relative to the shaft, and the catheter is advanced over the guidewire. The cutting device is actuated so as to expose a distal portion of the cutting device exterior of the catheter, and the orientation of the cutting device is fixed.

BRIEF DESCRIPTION OF THE DRAWINGS

The various objects, advantages and novel features of this invention will be more fully apparent from a reading of the following detailed description in conjunction with the accompanying drawings in which like reference numerals refer to like parts, and in which:

FIG. 1 is a plan view of one embodiment of apparatus constructed in accordance with this invention;

FIG. 2 is a cross-section taken along lines 2-2 in FIG. 1;

FIG. 3 is a cross-section taken along lines 3-3 in FIG. 2;

FIG. 4 is a cross-section taken along lines 4-4 in FIG. 2;

FIG. 8A is a plan view of a snap in handle connection for the apparatus of FIG. 8;

FIG. 10 is a detailed view of the rotation lock of FIG. 9;

FIG. 11 is a sectional view along line 11-11 of FIG. 10;

FIGS. 13A-D show alternative embodiments of the rotation lock of the present invention;

FIGS. 14A-D show cross-sectional areas of the alternate embodiment of FIGS. 13A-D;

FIG. 32 is a partial elevational view of another embodiment of the catheter in accordance with the present invention;

FIG. 32A is a cross-sectional view of the catheter of FIG. 32 taken along line 32A-32A;

FIG. 32B is a cross-sectional view of the catheter of FIG. 32 taken along line 32B-3213;

FIG. 33 is a partial elevational view of another embodiment of the catheter in accordance with the present invention;

FIG. 33A is a cross-sectional view of the catheter of FIG. 33 taken along line 33A-33A;

FIG. 33B is a cross-sectional view of the catheter of FIG. 33 taken along line 33B-33B;

FIG. 38 shows the thinned wall catheter of FIG. 37 positioned through an endoscope detailing the relationship of the guidewire and the catheter when a rapid exchange catheter is used; and FIG. 38A is a sectional view along line 38A-38A of FIG. 38.

DESCRIPTION OF ILLUSTRATED EMBODIMENTS

Figure 5:
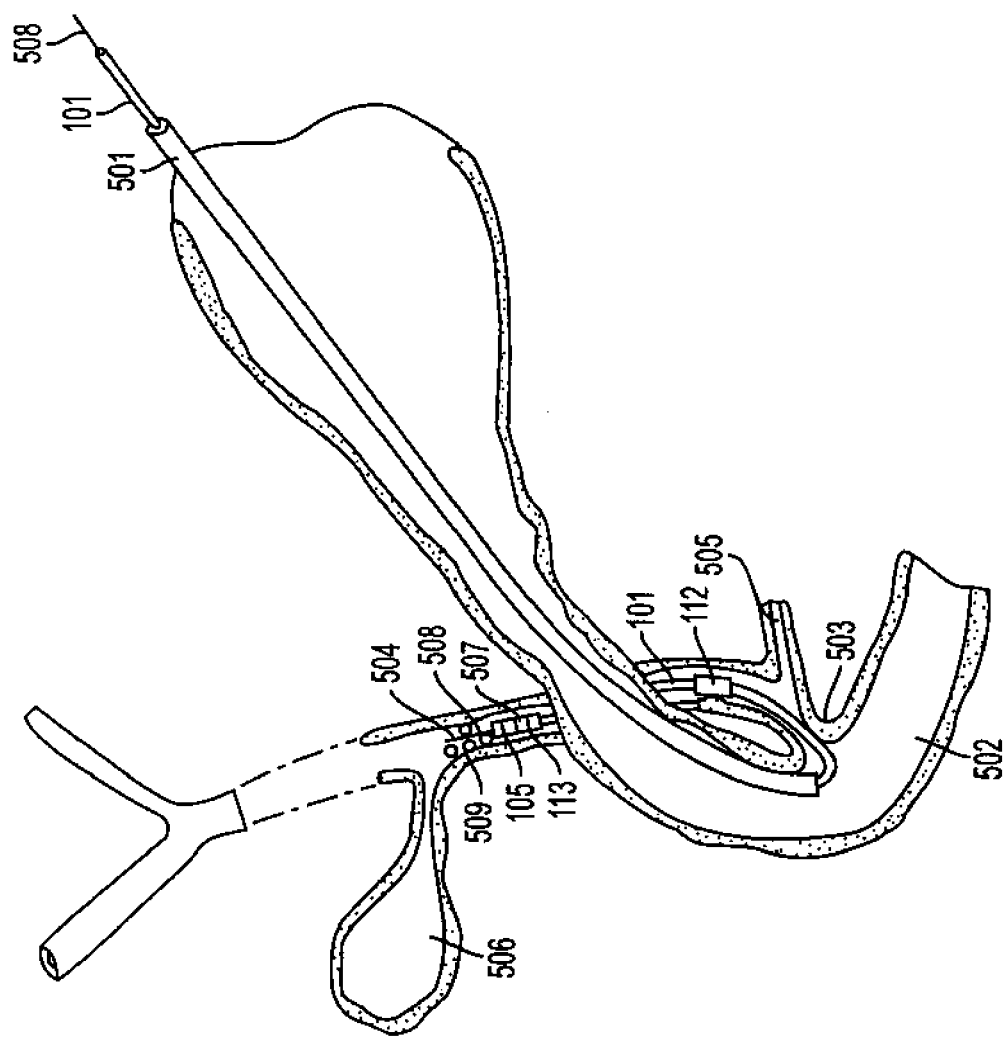
FIG. 5 depicts the apparatus of FIG. 1 positioned through a duodenoscope for injecting contrast agent into the biliary tree.

FIG. 1 depicts catheter apparatus 100 that has the capability of injecting a contrast agent into the biliary tree, accurately positioning and maintaining the position of a cutting wire, of performing a sphincterotomy and of dislodging a gallstone into the duodenum. Apparatus 100 includes a catheter 101 which, for purposes of definition, includes proximal portion 102 extending from proximal end 103 and distal end 104 with distal portion 105 extending a short distance proximally from distal end 104. In a typical application, catheter 101 will have a working length of 200 cm and distal portion 105 will have a length of 6 cm to 9 cm. Normally, distal portion 105 will have a diameter that is smaller than the diameter of proximal portion 102 to increase the flexibility of distal portion 105. The reduction in diameter also makes distal end 104 less traumatic and allows distal portion 105 to reach smaller passages while allowing the larger proximal portion 102 to provide necessary hoop strength and rigidity, particularly where proximal portion 102 is coextensive with the working channel of a duodenoscope. For example, the proximal and distal portions might have diameters corresponding to 7 Fr and 5.5 Fr catheter sizes (i.e., 0.09" and 0.07", respectively).

As shown particularly in FIG. 2, catheter 101 has three lumens. First lumen 201 has a diameter that is greater than either second lumen 202 or third lumen 203. In one particular embodiment, first lumen 201 has a diameter of 0.040" in proximal portion 102 that reduces to about 0.037" in distal portion 105 to receive a standard 0.035" guidewire. In addition, first lumen 201 is offset from the center of catheter 101. While FIG. 2 shows lumens of various diameters, the present invention may be implemented in a catheter which includes lumens of identical size.

The cross section of both second lumen 202 and third lumen 203 are shown smaller than the cross section of first lumen 201 and are radially offset from the centerline of catheter 101, from each other and from first lumen 201. In one particular embodiment, the cross section of third lumen 203 has a diameter of 0.028" in proximal portion 102 that reduces to about 0.020" in distal portion 105, and second lumen 202 has an internal diameter of 0.028" in proximal portion 102 that reduces to about 0.020" in distal portion 105. As described later, this third lumen 203 carries a cutting wire for performing a sphincterotomy and for allowing the infusion of a contrast agent at reasonable rates. The orientation of the cutting wire can also be positioned as desired as further described herein. The angular spacing between second lumen 202 and third lumen 203 is about 45 degrees, and the angular spacing between first lumen 201 and each of lumens 202 and 203 each is about 157.5 degrees. In this configuration and with these dimensions, proximal portion 102 readily passes through the working channel of any duodenoscope.

Referring again to FIGS. 1 and 2, each of lumens 201, 202 and 203 includes an entry port in proximal portion 102 and an exit port in distal portion 105. Generally, and as described in more detail later, first lumen 201 has an exit port through distal end 104, while the exit ports for lumens 202 and 203 can be sited at different locations in distal portion 105 depending upon a particular application.

In FIG. 1, the entry ports in proximal portion 102 adjacent proximal end 103 include an entry port 106 that provides access to first lumen 201 and includes an optional Luer lock fitting 107. Proximally positioned entry port 108 provides access to second lumen 202 and includes optional Luer lock fitting 109. Proximal entry port 110 for third lumen 203 is located coextensively with a portion of handle 111 attached to proximal end 103. One of ordinary skill in the art would understand that this specific configuration is given as an example and not meant to limit the invention. Various other configurations would be apparent to one of ordinary skill in the art to practice the invention described herein.

Referring to FIG. 3, the distal portion 105 of catheter 101 in this particular embodiment carries expansible balloon 112 proximally of the excursion of cutting wire 113 (FIG. 1) externally of catheter 101. Second lumen 202 emerges at distal exit port 301 through the side of catheter 101 with the interior of expansible balloon 112. An extension 302 of second lumen 202 beyond distal port 301 is sealed by known methods of manufacture. Consequently, fluid forced through entrance port 108, as by a syringe (not shown) attached to Luer lock fitting 109, expands balloon 112 into an occluding orientation with an inflated diameter in the range up to 20 mm.

First lumen 201 extends through catheter 101 and terminates with exit port 303 in distal end 104. Thus first lumen 201 is adapted for receiving a guidewire through the entry port 106 that will extend through catheter 101 and exit via exit port 303 in distal end 104 and allow the catheter to slide over that guidewire.

Referring to FIG. 4, distal end 401 of cutting wire 113 attaches to a clamp 402 formed at the distal end of third lumen 203. Spaced skived ports 403 and 404 allow active portion 405 of the cutting wire 113 to emerge from catheter 101 through skived aperture 403, parallel catheter 101 exteriorly thereof, and return into third lumen 203 through port 404 and reinforcing sleeve 406. Cutting wire 113 then extends through third lumen 203 to handle 111 shown in FIG. 1 where it emerges as proximal end portion 114.

Figure 6:
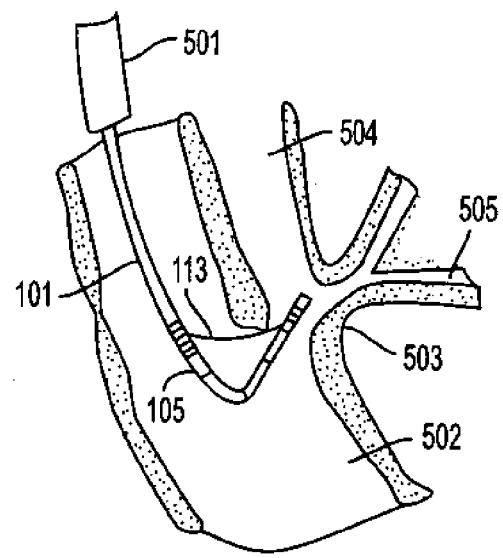
FIG. 6 is an enlarged view that depicts the orientation of the apparatus in FIG. 1 for performing a sphincterotomy.

Handle 111, as shown in FIG. 1, includes central member 115 terminating with thumb ring 116. Central member 115 extends through and slides with respect to body section 117 having opposed finger rings 118. Central member 115 also attaches to catheter 101 at catheter hub assembly 122 and is therefore an extension of catheter 101. Body section 117 additionally includes internal connector 119 for clamping proximal end 114 of cutting wire 113. Thus, when body section 117 is at its distal position as shown in FIG. 1, distal portion 105 of catheter 101 is in essentially a straight line as shown in FIG. 1 and FIG. 4 with active portion 305 of cutting wire 113 being closely adjacent catheter 101. Retracting body section 117 causes cutting wire 113 to bend distal end 104 upwardly as shown in FIG. 6 to a position that is essentially at right angles to the main axis of the catheter, as will be shown later.

Internal connector 119 and cutting wire 113 are generally conductive members that attach through RF connector 120 to RF heating source 121. The use of such RF heating sources 121 for energizing cutting wire 113 thereby to cut the sphincter muscle is well known in the art and represents one possible sphincterotomy procedure that can be adapted for the apparatus of this invention and is not described further. RF connector 120 is also known as an active cord attachment, and the cord from the RF heating source may be referred to as an active cord.

With this description of the apparatus structure, it will now be possible to understand its use in a particular application. FIG. 5 discloses, in a partially broken and schematic view, the positioning of duodenoscope 501 in duodenum 502 adjacent sphincter of Oddi 503. Catheter 101 such as constructed in FIG. 1 passes through sphincter of Oddi 503 into the common bile duct 504, bypassing pancreatic duct 505. Distal end 104 does not extend to gallbladder 506.

Fluoroscopy allows the appropriate positioning by utilizing a series of radio-opaque markers 507 at distal portion 105 that may include clamp 402 and reinforcing sleeve 406 in FIG. 4. Catheter 101 can be positioned with or without the presence of guidewire 508 in first lumen 201 shown in FIGS. 5, and 7. For purposes of injecting the contrast agent, any guidewire 508 can be withdrawn to allow the contrast agent to be injected through first lumen 201 for purposes of fluoroscopic examination to confirm the presence of one or more gallstones 509. It is also possible during the operation to expand balloon 112 to occlude common bile duct 504 and block any migration of contrast agent into duodenum 502 or pancreatic duct 505.

FIG. 6 is an enlarged view showing duodenum 502, sphincter of Oddi 503, portions of pancreatic duct 505 and common bile duct 504. In FIG. 6, catheter 101 has been positioned relative to the duodenoscope 501 through the opening of sphincter of Oddi 503. Body section 117 of handle 111 in FIG. 1 has been drawn proximally to deflect distal portion 105 into essentially a right angle configuration such that cutting wire 113 abuts a portion of sphincter of Oddi 503. The application of RF heating to cutting wire 113 then will cut sphincter of Oddi 503 and enlarge the opening therethrough. As will be apparent, the sphincterotomy is performed with direct visualization of the sphincter of Oddi 503 through duodenoscope 501.

Moreover, as has been observed by others, catheters having guidewire and cutting wire lumens tend to assume a particular angular orientation when distal portion 105 emerges from the duodenoscope. This orientation is essentially independent of the angular position of the catheter when it is inserted into duodenoscope 501. The offset nature of lumen 203 as shown in FIG. 2, improves the location of cutting wire 113 as distal portion 105 passes through sphincter of Oddi 503. Specifically, the angularly offset brings cutting wire 113 into better alignment with common bile duct 504 and displaces the cutting wire from pancreatic duct 505.

Figure 7:
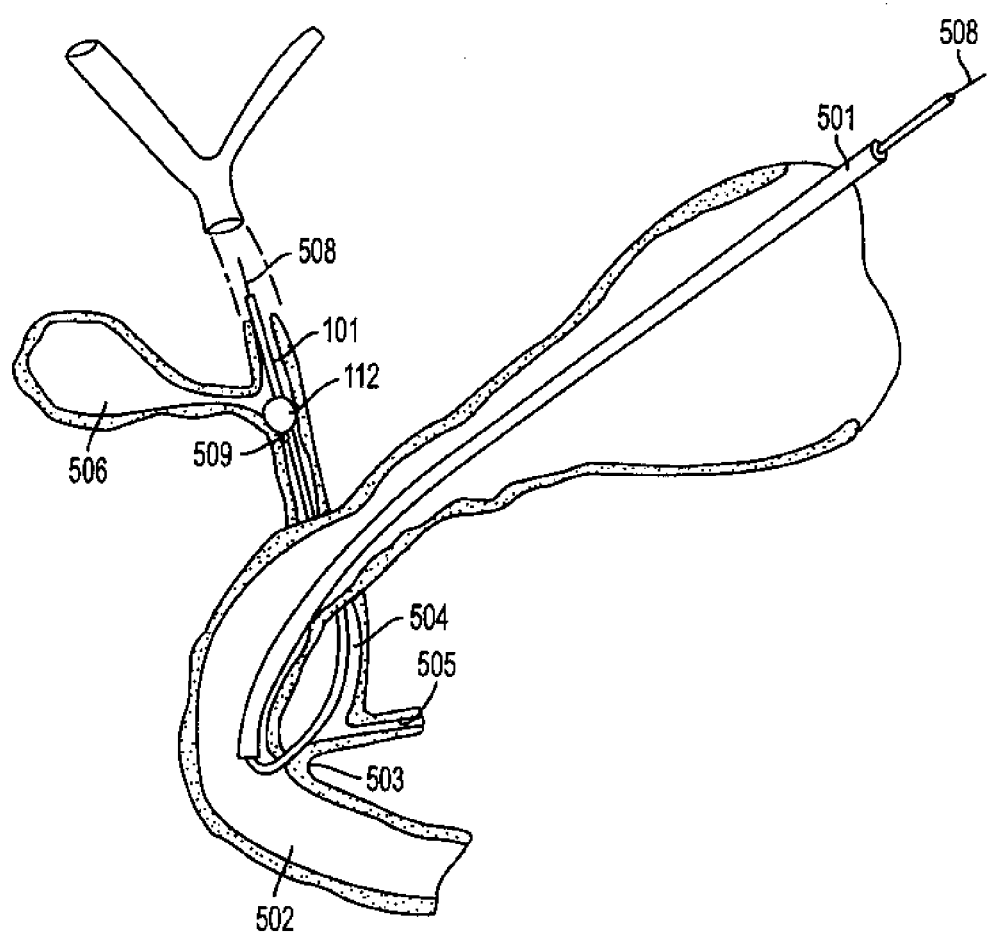
FIG. 7 depicts the apparatus of FIG. 1 positioned through a duodenoscope for dislodging material within the common bile duct.

FIG. 7 depicts the catheter after the sphincterotomy and after catheter 101 is advanced over guidewire 508, if used. FIG. 7 also discloses catheter 101 after balloon 112 has been moved beyond gallstone 509 in bile duct 504. Balloon 112 is expanded so that upon withdrawal of catheter 101 balloon 112 will dislodge gallstones 509 and sweep them through sphincter of Oddi 503 into duodenum 502.

One of ordinary skill in the art would appreciate that the present invention would include switching the orientation of balloon 112 and cutting wire 113. In other words, FIGS. 1, 3 and 4 illustrate an embodiment in which balloon 112 is located proximally of cutting wire 113. In an alternative embodiment of the present invention, the balloon may be located distally of the cutting wire. One of ordinary skill in the art would also appreciate that the location of the exit ports for the various lumens may be sited at different locations in distal portion 105 depending upon the particular application. For example, second lumen 202 may have an exit port located in distal end 104 of distal portion 105. This configuration may be desirable for injecting contrast agent directly into the biliary tree while the guidewire remains in place in first lumen 201.

As one of ordinary skill in the art would appreciate, proper positioning of the endoscopic instrument, such as cutting wire 113, is crucial in the proper treatment of obstructive disease. As explained above, catheters having guidewire and cutting wire lumens tend to assume a particular angular orientation when distal portion 105 emerges from duodenoscope 501. Since this orientation is essentially independent of the angular position of the catheter when it is inserted into duodenoscope 501, a need exists to properly position cutting wire 113. Safe and effective results are only obtained through precise positioning of cutting wire 113 and control or maintenance of the portion of the exposed cutting wire.

Due to inconsistencies in the sphincterotome, anatomy, and endoscope manipulation, it is difficult to accurately and consistently position the sphincterotome for proper cannulation. The steerable sphincterotome of the present invention allows the physician to control the position of distal end 104 of the device independently of the endoscope and adjust for inconsistencies in the device and the anatomy. According to the present invention, handle 111 to which cutting wire 113 is attached is freely rotatable relative to catheter 101. Rotating handle 111 of the present invention induces a twisting of attached cutting wire 113, which allows orientation of distal end 104 without rotating proximal end 103 of attached catheter 101.

Figure 8:
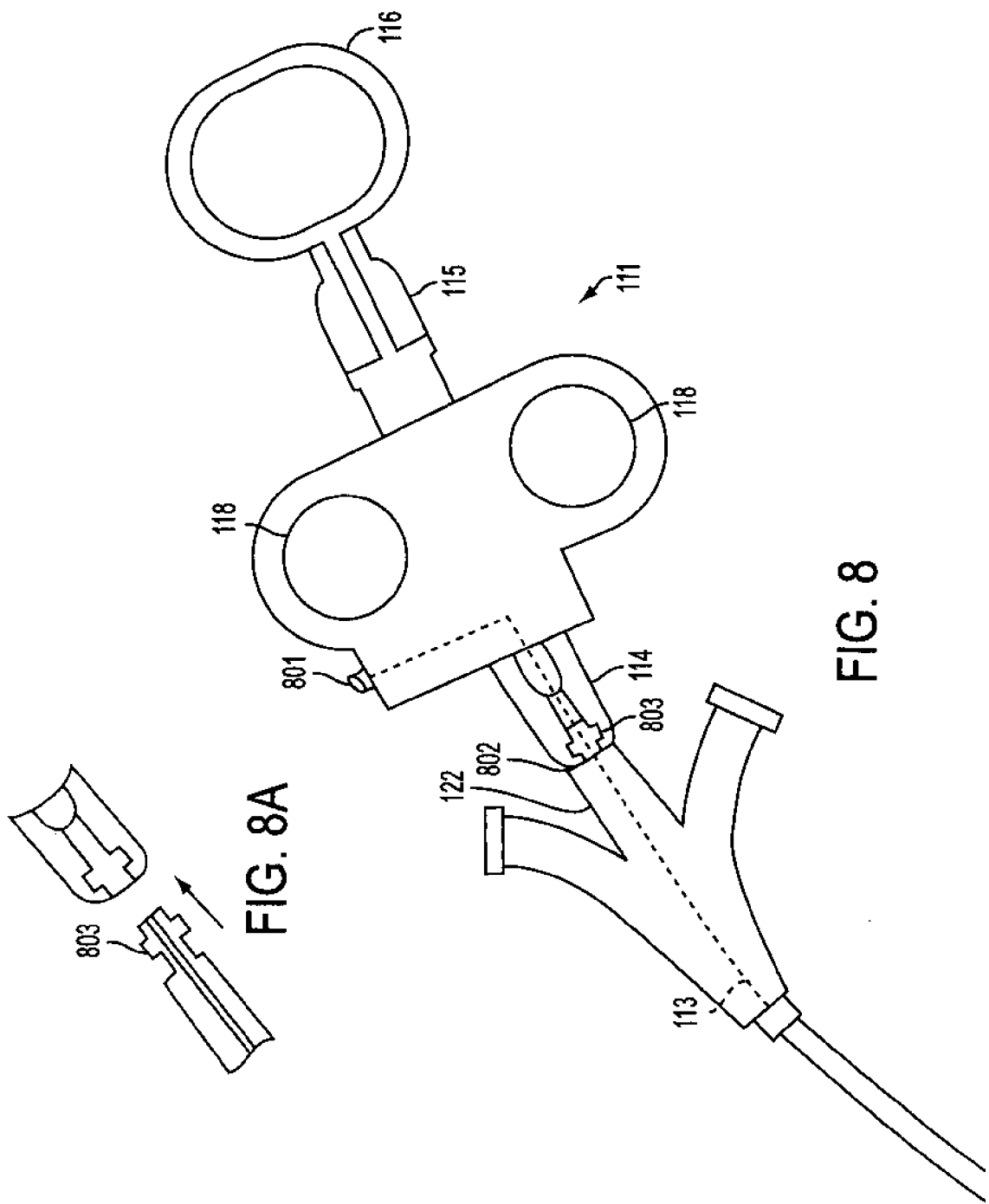
FIG. 8 is a plan view of one embodiment of apparatus constructed in accordance with the present invention with a rotatable handle attached to a cutting wire.

FIG. 8 shows handle 111 secured to cutting wire 113 at 801 but rotatable relative to the catheter hub assembly 122 at 802. This configuration provides a mechanism to rotate cutting wire 113, thereby transmitting a force used to rotate device end 104. With handle 111 rotating independently of catheter hub assembly 122 at proximal end 103, the force can be applied directly to distal end 104 without twisting the entire shaft. A rotation lock may be included to maintain the orientation of the tip and a rotation marking may be included to indicate the amount of rotation present. An integrated molded luer port assembly 803 for two and three lumen catheters may be provided to snap into rotatable handle 111 to facilitate fast and economical manufacturing, as shown in FIGS. 8 and 8A.

Figure 9:
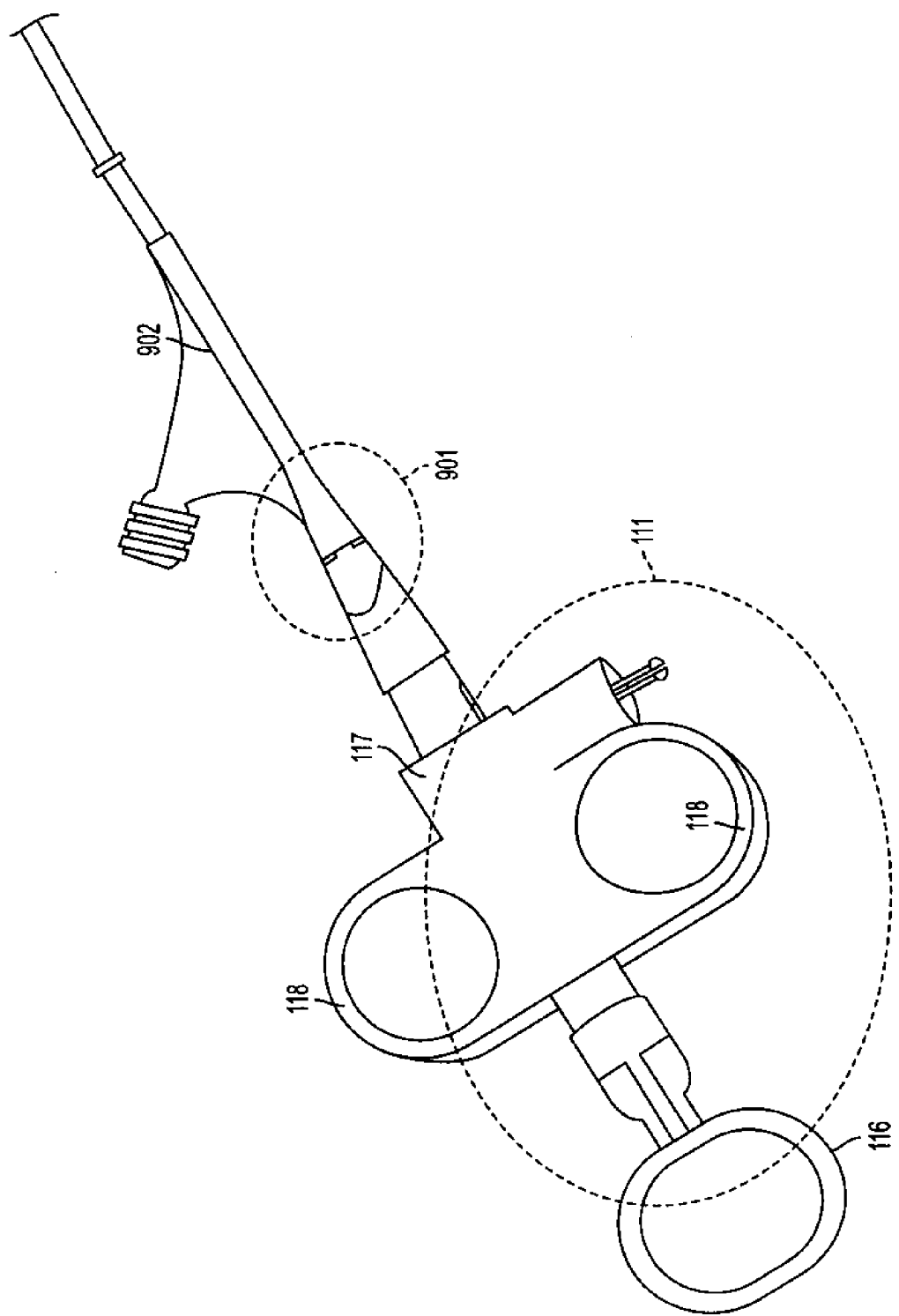
FIG. 9 is a view of the rotatable handle of the present invention including a rotation lock.

FIG. 9 shows a rotation lock of the present invention. Rotation lock 901 enables the user to maintain the orientation of distal end 104. One method of maintaining the orientation of distal end 104 is to maintain the position of handle 111 relative to bifurcation connector 902 after handle 111 has been rotated. Rotation lock 901 allows the user to release handle 111 at any time during the procedure, while maintaining the orientation of handle 111 and preventing further rotation while rotation lock 901 is engaged. Maintaining the position of handle 111 maintains the orientation of distal end 104 in the desired orientation. Maintaining the orientation of the distal end 104 reduces the amount of time and effort required to cannulate if distal end 104 moved. Preventing undesired movement of distal end 104 may also prevent patient injury. With respect to rotation of handle 111, one of ordinary skill in the art would appreciate that body section 117 rotates with handle 111, and handle 111 is used as a shorthand when discussing rotation.

FIG. 10 shows two pair of mating detents 1001 and slots 1002 which may be used to create rotation lock 901. Detents 1001 and slots 1002 are located along the central axis of body section 117 at the intersection of body section 117 and bifurcation connector 902. In FIG. 10, the two pair of detents 1001 and slots 1002 are located 180° apart relative to the central axis. This configuration creates a lock position every half rotation of handle 111. During use of the device, as handle 111 is rotated, detents 1001 become disengaged from slots 1002. As detents 1001 become disengaged, they compress slightly. As handle 111 reaches a position 180° from where rotation began, detents 1001 recover from their compressed state, and engage with slots 1002 once again. As detents 1001 traverse from one position to the next, there is a noticeable amount of friction between the mating components. This friction is great enough that handle 111 can be released at any time without fear of losing the orientation position of distal end 104.

Rotation lock 901 also serves a secondary function of keeping distal end 104 locked in the home position while catheter 101 is being removed from the package, inserted into the endoscope, and manipulated through the endoscope. Without this feature, the initial orientation position of distal end 104 would become unpredictable. FIG. 11 shows a detailed diagram of the interaction between detents 1001 and slots 1002.

Figure 12:
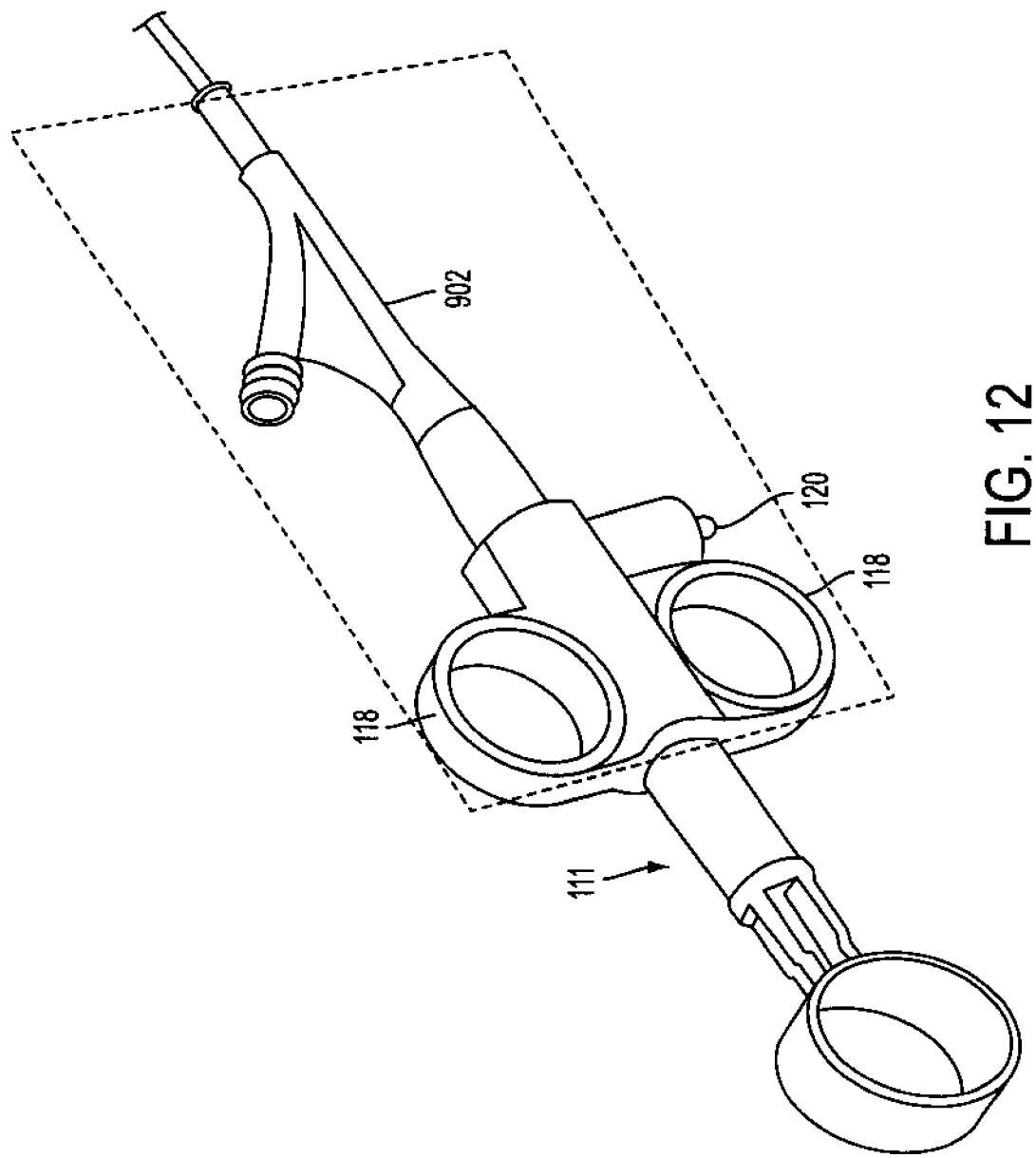
FIG. 12 shows an alignment between the rotatable handle and the bifurcation connector showing zero rotation of the rotatable handle.

Referring to FIG. 12, when detents 1001 and slots 1002 are engaged, bifurcation connector 902 and finger rings 118 all lie in the same plane. This acts as a rotation marker. When finger rings 118 are rotated into the same plane as bifurcation connector 902, the rotation lock is engaged, thus signaling 180° of rotation from the last position. The use of a marker such as this allows the user to more easily keep track of how much handle 111 has been rotated. This is helpful if the user desires to move distal end 104 back to its original position. In effect, the user will know, for example, that handle 111 has been rotated three clicks from the original position. Therefore, to return handle 111 to the original position, it must be rotated three clicks in the opposite direction.

FIGS. 13A-13D show alternative embodiments of rotation lock 901. FIG. 13A shows a pure frictional lock. The connection of bifurcation connector 902 to handle 111 could be designed such that rotation lock 901 is purely a function of frictional interference between the two components. Alternative embodiments could include different types of assembly joints to create this friction. In the primary embodiment, the assembly of the two components is accomplished by mating a post or protrusion of the bifurcation connector to a hole of the same size and shape. Alternative embodiments could reverse this, so that a post or protrusion is part of the main body of handle 111. The friction lock could also be built into the mating faces of main body and bifurcation connector, which are perpendicular to the major axis. FIG. 14A shows a cross section of rotation lock 902 along 14A-14A of FIG. 13A.

FIG. 13B shows an oval post lock embodiment of the present invention. The connection of bifurcation connector 902 to handle 111 could also be designed incorporating an ovalized post 1301 and hole 1302. In this embodiment, as handle 111 is rotated relative to bifurcation connector 902, ovalized hole 1302 would deform, allowing oval post 1301 to rotate. As handle 111 reached a rotation of 180°, ovalized hole 1302 would conform back to its original shape, thus locking handle 111 in place. As shown in FIGS. 13C and 13D, this basic concept may be expanded to incorporate other shapes rather than oval as shown in FIG. 13B. One of ordinary skill in the art would appreciate that the shape of the geometry, however, governs the degrees of rotation between locked positions. For example, if post 1301 and ovalized hole 1302 configuration were made up of mating equilateral triangles (FIG. 13C), there would be 120° of rotation between locked positions. Using a square configuration (FIG. 13D), would give 90° between locked positions. FIG. 14B illustrates the cross-sectional area across 14B-14B of FIG. 13B. FIG. 14C illustrates the cross-sectional area of FIG. 13C across 14C-14C, and FIG. 14D illustrates the cross-sectional area of FIG. 13D along cross-section 14D-14D.

Figure 15A:
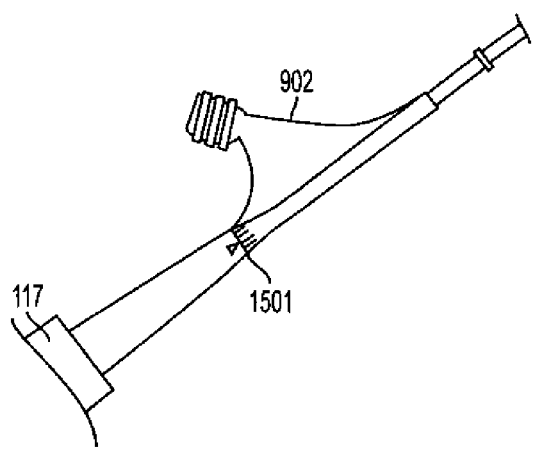
FIGS. 15A-C show three alternative embodiments of rotation markings for the present invention.
Figure 15B:
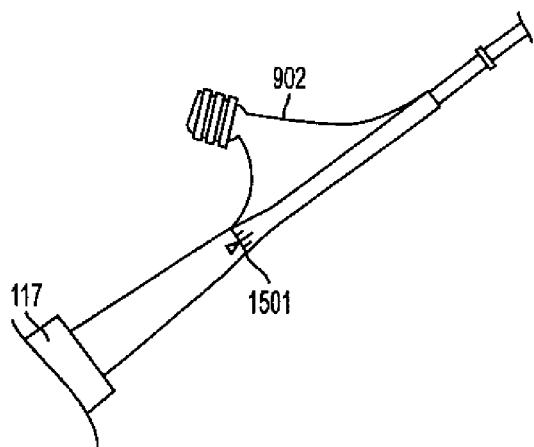
Figure 15C:
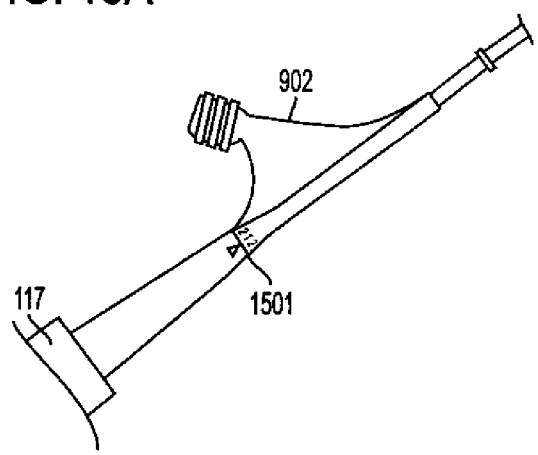

FIGS. 15A-C show alternative embodiments by which a rotation marker 1501 may be created and included in the present invention. One of ordinary skill in the art would understand these embodiments may be expanded. To aid the user in knowing exactly how much handle 111 has been rotated from its original and/or last position, several forms of visual markers can be incorporated into the design. One alternative embodiment is comprised of a set of lines placed radially, around the major axis, at the area where body section 117 and bifurcation connector 902 meets (FIG. 15A). A single line on the stationary component, bifurcation connector 902, would match up with a corresponding line on body section 117. As handle 111 is rotated relative to bifurcation connector 902, the series of lines or arrows on body section 117 would rotate past the stationary line on bifurcation 902. Each line would indicate an incremental amount of movement. For example, if there were four, equally spaced lines on the body, each line that passed the marker on the bifurcation connection would signify 90° of rotation.

This feature could be further enhanced by many methods. A series of numbers rather than lines could be used to signify the amount of rotation (FIG. 15C). Alternating colors could also be used to signify the amount of rotation. Alternating line patterns could be used as well (FIG. 15B).

Another alternative embodiment may use audible tones such as clicks to make the user aware of the amount of rotation. One method of incorporating this feature may be to design the rotation lock features so that a click is clearly audible at predetermined points along the rotational travel of the body. One of ordinary skill in the art would also appreciate that there are several alternative means by which a connector can be created and that each of these alternatives is included in the present invention. One of ordinary skill in the art would also appreciate that the connector design of the present invention could easily be modified to accommodate three or more lumens.

Figure 16A:
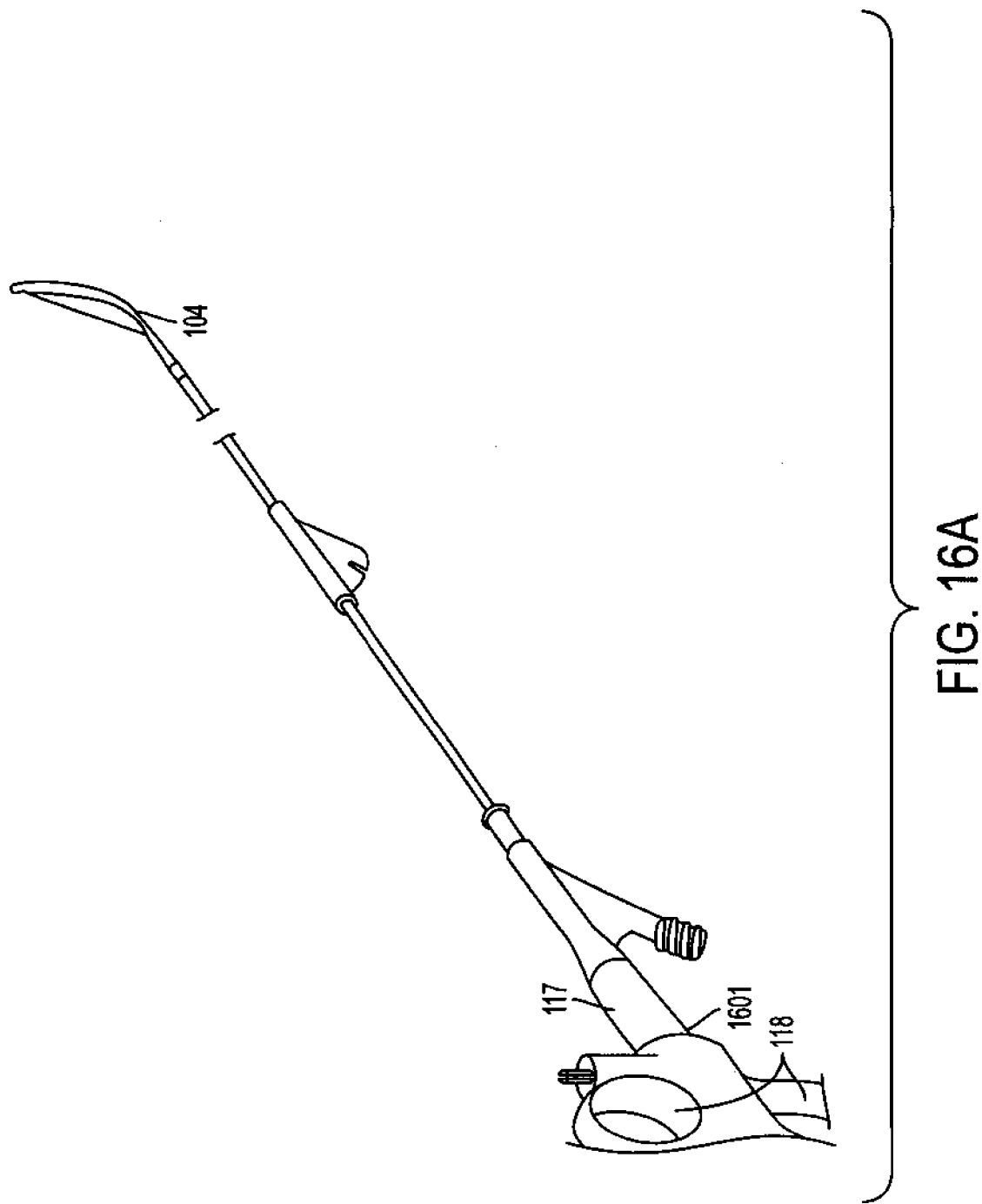
FIGS. 16A and B illustrate a bowing lock included in the present invention.

FIGS. 16A and B show additional embodiments of the present invention which may include handle 111 similar to that previously described, but with the addition of a bowing lock. A bowing lock would aid the user in that handle 111 could be released at any time and at any orientation, and distal end 104 would maintain its bowed position. Just as rotation lock 901 provides for a safer and more efficient procedure, the bowing lock would perform similarly. The bowing lock could be incorporated into the design in many ways. The bowing lock, in its simplest form, would consist of friction lock 1601 created between finger rings 118 and body section 117 (FIG. 16A). An alternative to this design would create a similar friction lock, but would use the surfaces between wire termination 1602 and body section 117 (FIG. 16B). The friction lock shown in FIG. 16B is enhanced by incorporating several lock ribs 1603. Lock ribs 1603 would be used to hold distal end 104 at a specific, predetermined angle. In effect, locking handle 111 into the first position would, for example, deflect the tip 30°. The next position would, for example, deflect the tip 60°, This feature would give the user even more control when positioning distal end 104 within the anatomy. In both cases, as finger rings 118 are actuated along body section 117, and distal end 104 is bowed, the friction between the mating components would hold the position of handle 111, and thus hold the position of the bow.

FIGS. 17-20 show various configurations of an alternate embodiment of the present invention for maintaining the position of an endoscopic instrument. In each of these configurations, the actuation of various handle assemblies has been modified to include an insert which provides a minimal amount of resistance. The resistance added to each of these configurations resists movement of the device away from a set or desired position. Each of the embodiments adds friction to the handles by means of placing a frictional element which provides interference between the moving parts. The interference provides a light braking force which resists movement in the distal end of a device without user intervention when the device is actuated by means of a handle. Each of the embodiments includes a frictional element composed of rubber, silicone, or other suitable material which provides the desired braking force. The minimal interference of the frictional element ensures that the interference does not prevent the continuous smooth movement of the handle actuators present during normal operation of the handle. In a preferred embodiment of the invention, the frictional elements described resist undesired movement in the distal end without requiring the user to engage, set or actuate a locking mechanism.

Figure 17:
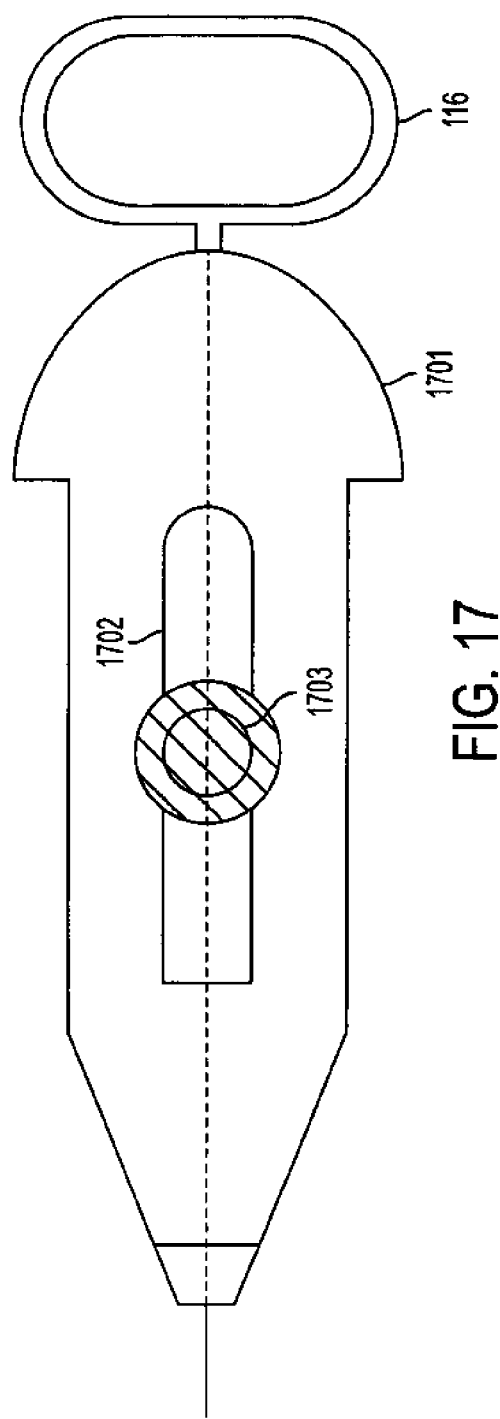
FIG. 17 shows a handle of a Rapid Exchange Tome including an insert to resist movement.

FIG. 17 shows a handle 1701 of a Rapid Exchange Tome. Attached to handle 1701 is thumb ring 116. In operation, handle 1701 slides within body section 117 (not shown). Typically, a post or internal feature of body section 117 (not shown) translates within handle cutout 1702. Insert 1703 resides within handle cutout 1702 and preferably protrudes outwardly from handle 1701. The portion of insert 1703 which protrudes out of handle 1701 preferably makes contact with body section 117 and resists motion of body section 117 with respect to handle 1701. One of ordinary skill would appreciate that both the composition of insert 1703 and the distance insert 1703 protrudes out of handle 1701 are factors in the amount of resistance felt in moving body section 117 with respect to handle 1701.

Figure 18:
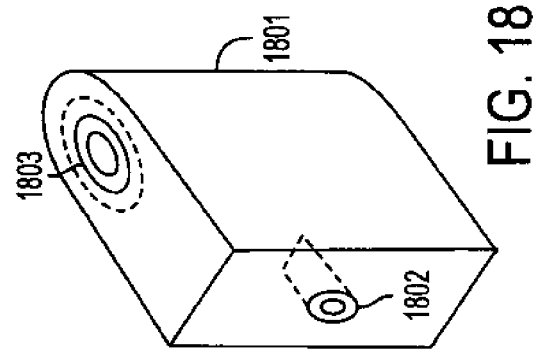
FIG. 18 shows an Ultratome "D" connector incorporating an insert to resist movement.
Figure 19:
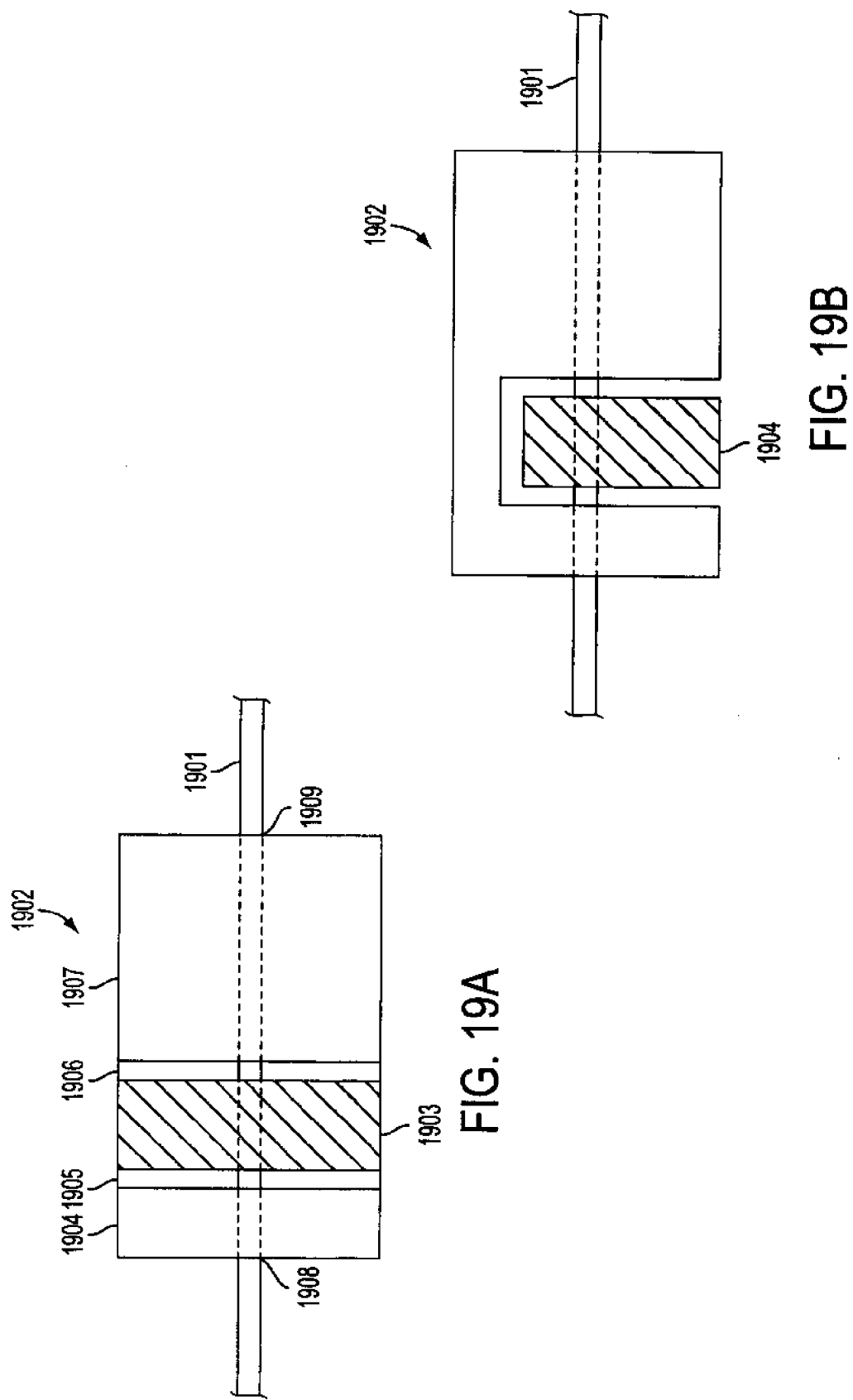
FIGS. 19A and B show two embodiments of inserts included in a Tome handle to prevent movement.

FIG. 18 shows a "D" connector 1801 of an Ultratome. The incorporation of inserts at position 1802 and 1803 are used to resist movement of items, such as surgical instrument passing through the inserts.

FIGS. 19A and B show two different embodiments of a soft brake for a Tome Handle. In both configurations, wire 1901, such as a guidewire, passes through a D-connector 1902. D-connector 1902 may be modified as shown to include an insert or stopper. FIG. 19A shows a rubber stopper 1903 which spans the height of D-connector 1902. As one of ordinary skill in the art would appreciate, wire 1901 enters D-connector 1902 at wire entrance 1908. Wire 1901 then passes through first section 1904 of D-connector 1902. Next, wire 1901 passes through first interface 1905 between D-connector 1902 and insert 1903. Wire 1901 then passes through insert 1903. Similarly, once wire 1901 exits insert 1903, wire 1901 passes through second interface 1906 and a wider section 1907 of D-connector 1902. The passage of wire 1901 through insert 1903 resists movement of wire 1901. FIG. 19B shows a similar configuration of insert 1904, except that insert 1904 is included in only a section of the vertical portion of D-connector 1902. One of ordinary skill in the art would appreciate that wire 1901 must pass through a section of insert 1904 to allow insert 1904 to resist movement in wire 1901.

Figure 20:
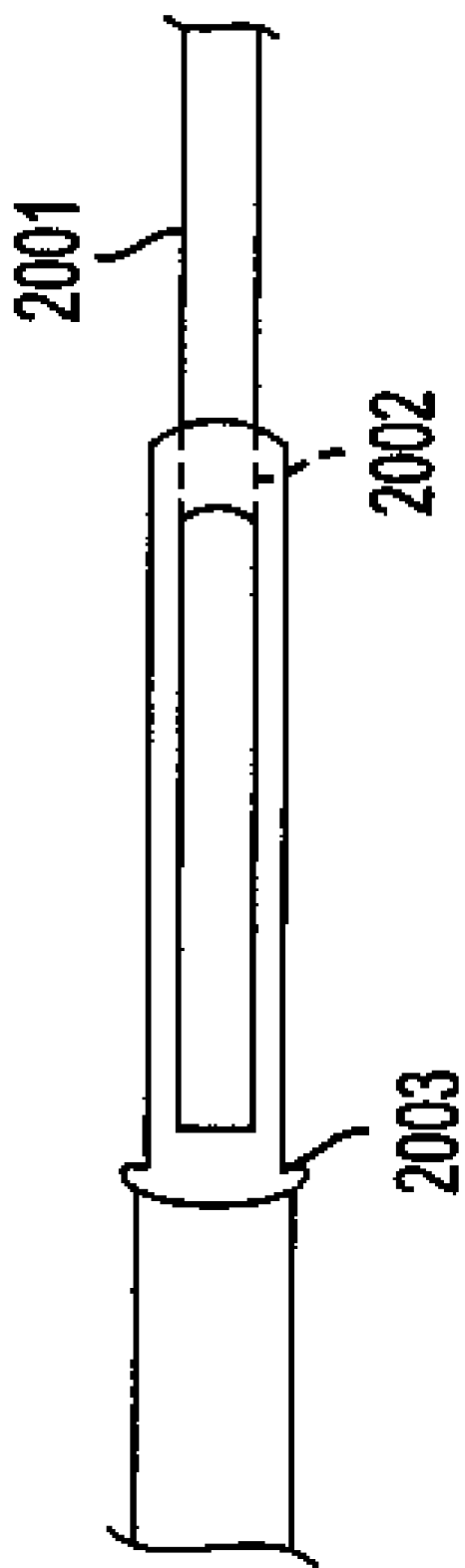
FIG. 20 shows an insert included in a body or handle to prevent movement.

FIG. 20 shows another embodiment of the soft brake of the present invention. In this embodiment, wire 2001 passes through bushing 2002 held within handle 2003. In this configuration, the circumferential friction applied to wire 2001 from bushing 2002 will resist wire 2001 movement.

Figure 21:
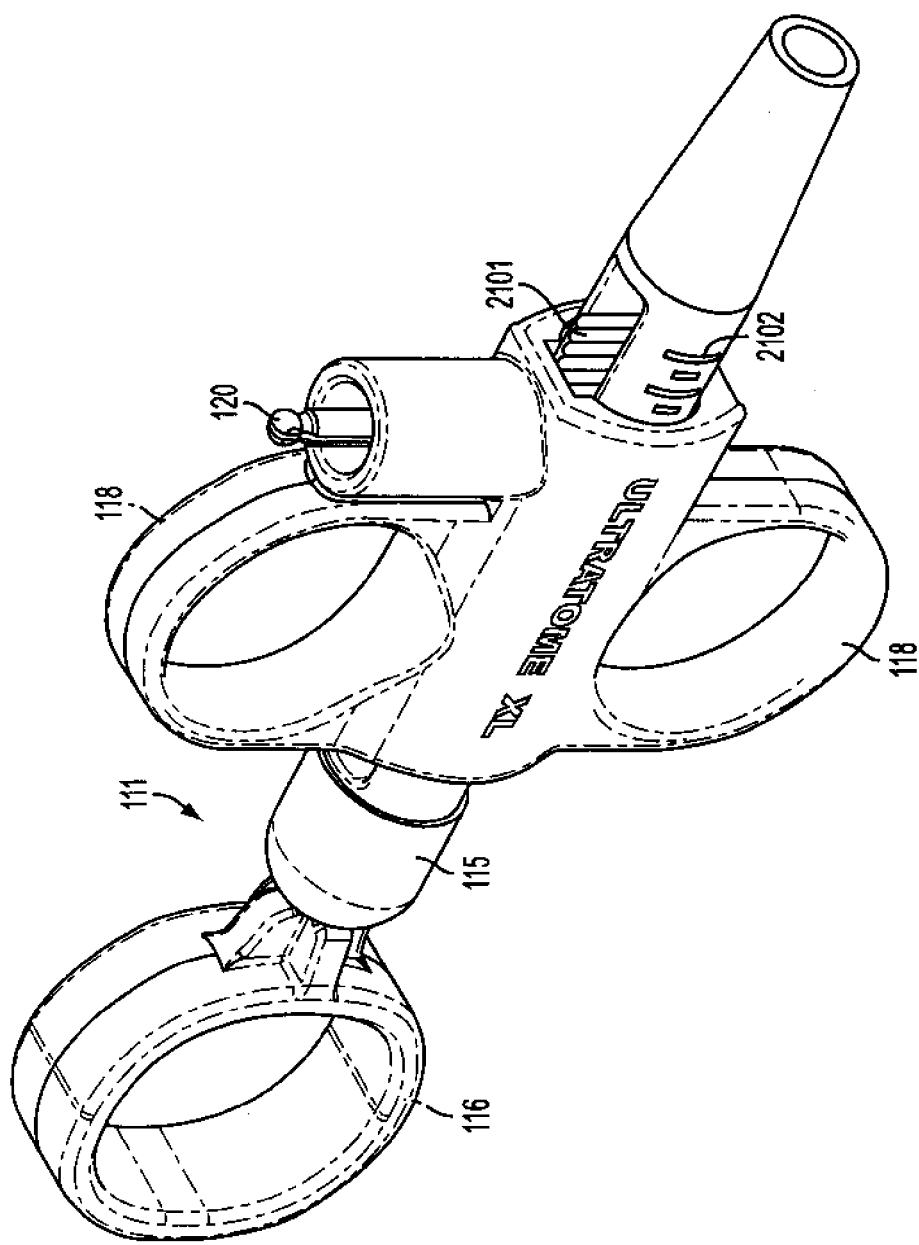
FIG. 21 shows an Ultratome XL handle including detents to prevent movement.
Figure 22:
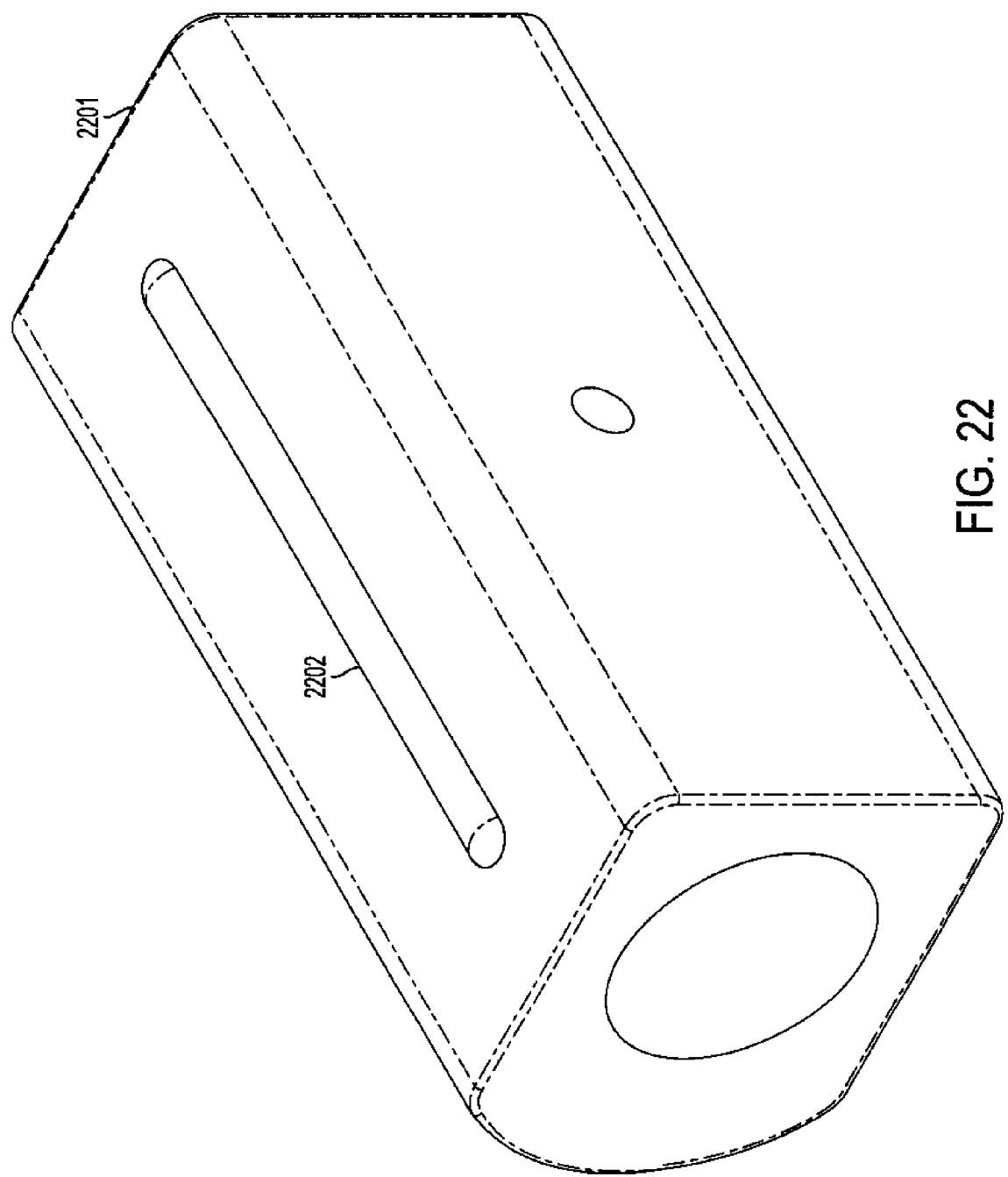
FIG. 22 shows an active cord insert which includes a pawl which cooperates with the handle of FIG. 21 to prevent movement.
Figure 23:
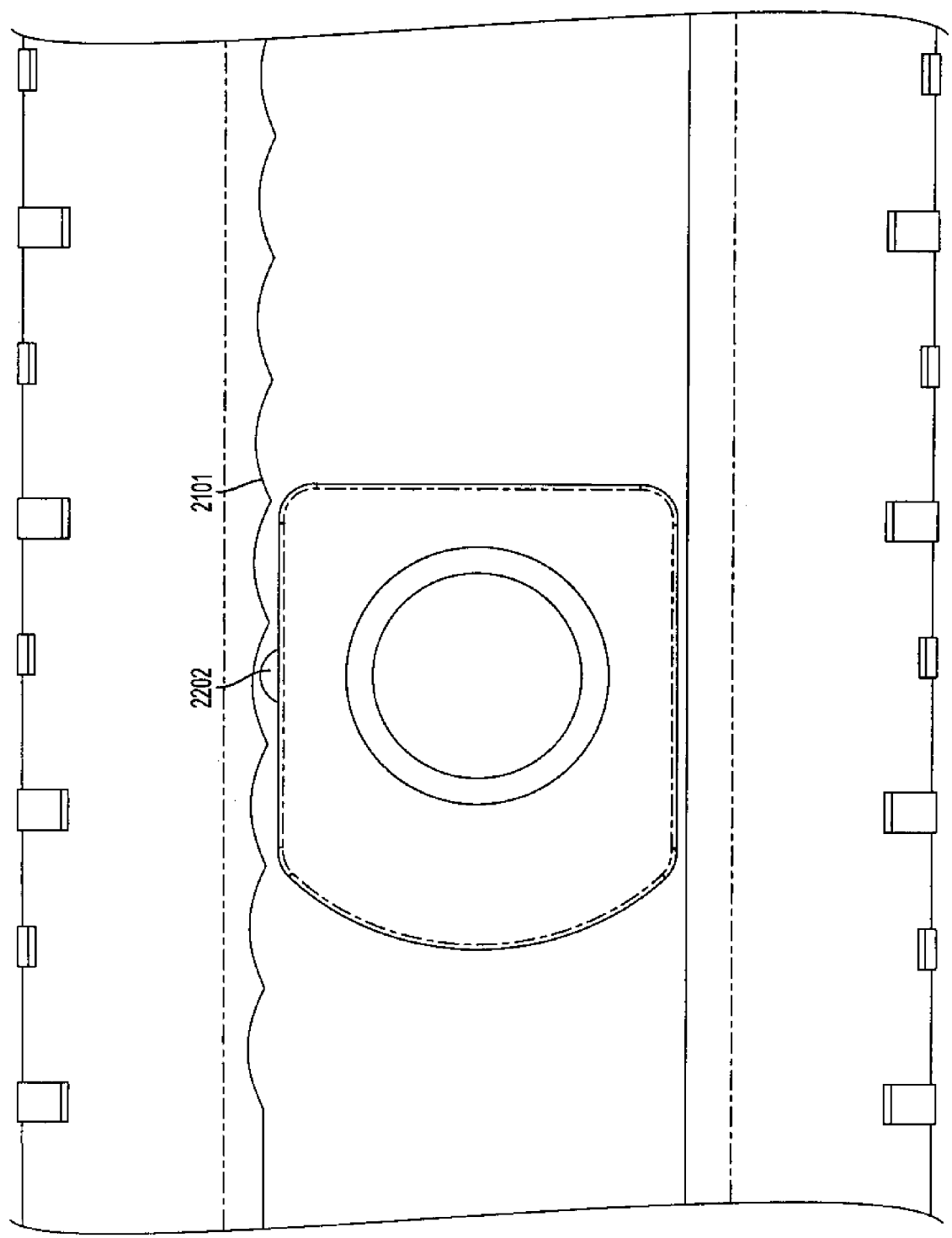
FIG. 23 shows the interaction of the detents of FIG. 21 and pawl of FIG. 22 to prevent movement.

FIGS. 21 through 23 show an alternate embodiment of the present invention in which a Tome-Loc handle design allows for the precise positioning and maintenance of the bow angle of a sphincterotome, or similar device, during the cutting procedure. This embodiment may be used to reduce or eliminate set relaxation. The design uses evenly spaced detents 2101 (FIG. 21) machined, or otherwise formed, in handle body 111 that capture a raised bump or pawl 2202 (FIG. 22) in the active cord insert 2201 (FIG. 22) and hold pawl 2202 or sprag in place. One of ordinary skill in the art would appreciate that detents 2101 may be also be molded into handle body 111. Detents 2101 may also be combined with graduation marks 2102 on the outside of handle body 111 to visually aid bow positioning. The modulus of elasticity of handle 111 acts as a spring to contain pawl 2202. When the device is actuated, handle body 111 flexes out and allows pawl 2202 to move on to the next detent with some slight resistance or a click. The interaction between detent 2101 and pawls 2202 would allow the lock to be automatic without requiring additional buttons or levers to be articulated by the user and may be implemented to maintain a predictable feel without introducing difficulty in the manipulation of the device. FIG. 23 shows an interaction of detents 2101 with pawl 2202. One of ordinary skill in the art would appreciate that the placement of detents 2101 on handle body 111 and pawls 2202 on active cord insert 2201 could be reversed in that detents could be placed on active cord insert (not shown) and pawls on handle body 111 (not shown). One of ordinary skill in the art would also appreciate that pawl 2202 need not necessarily be a hemispherical design but could also be a bar type or any type of configuration which would resist movement and locate into holes in handle body 111 to facilitate the detent feature. The basic design would rely on the same principals previously described.

Figure 24:
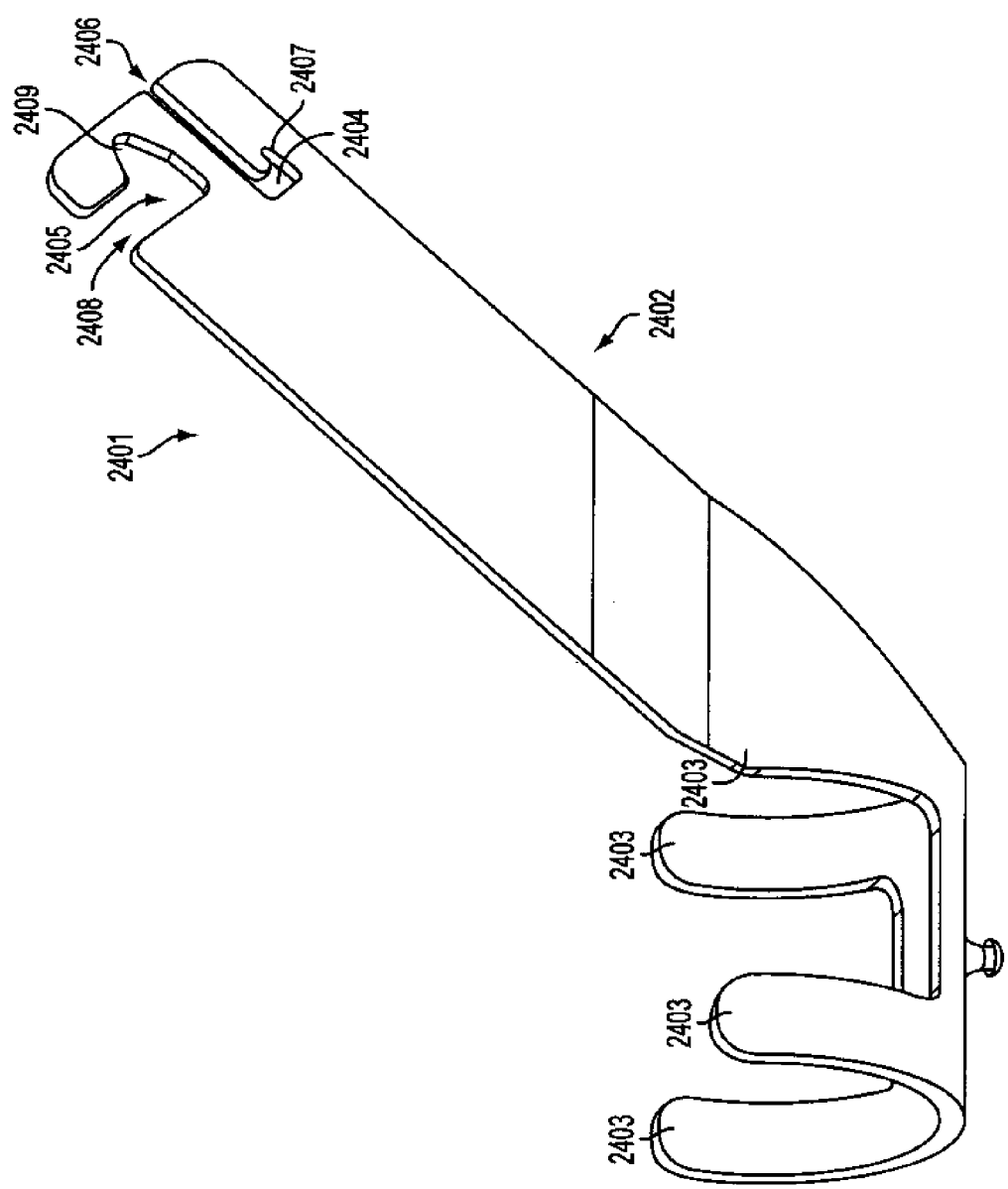
FIG. 24 is a perspective view of an illustrative locking device.
Figure 27:
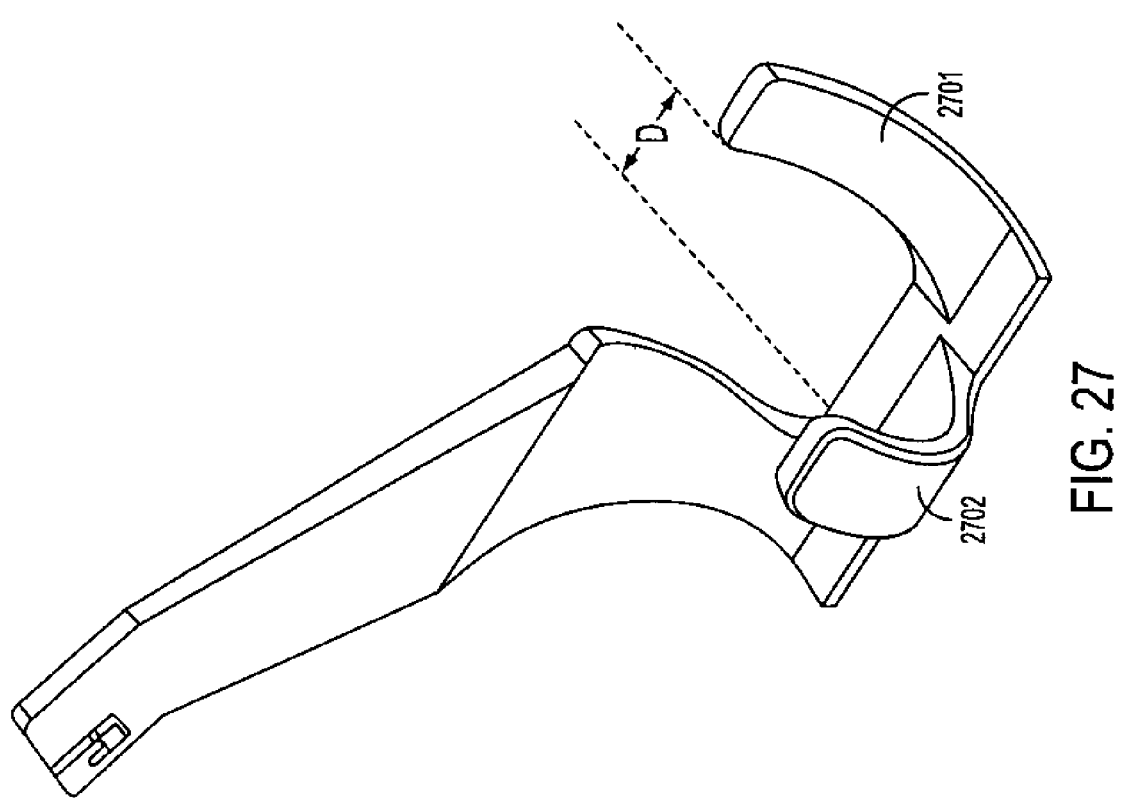
FIG. 27 is a perspective view of another illustrative locking device.

FIG. 24 is a perspective view of an illustrative locking device 2401 for use with an endoscope having a side instrument port. The illustrative locking device is generally shown at 2401 and includes a body member 2402. At one end, body member 2402 includes one or more hook members 2403 for attaching locking device 2401 to a shaft of an endoscope or the like (see FIG. 25). At the other end, body member 2402 includes a securing mechanism for securing a guide wire or catheter to to locking device 2401. Hook members 2403 may be provided in pairs, as shown in FIG. 24, or offset from one another, as shown in FIG. 27. In either case, hook members 2403 are adapted to clip and secure locking device 2401 to the shaft of an endoscope or the like. The securing mechanism preferably includes one or more openings provided in body member 2402. In the embodiment shown, body member 2402 includes a guide wire opening 2404 and catheter opening 2405. Guide wire opening 2404 is preferably J-shaped, and preferably includes entry slot 2406 and locking slot 2407. Catheter opening 2405 is boot shaped, and also preferably includes entry slot 2408 and locking slot 2409.

Entry slot 2406 of guide wire opening 2404 is dimensioned to be larger than the diameter of a guide wire. Locking slot 2407 of guide wire opening 2404 is dimensioned to be somewhat smaller than the diameter of a guide wire. Accordingly, a guide wire can be secured to body member 2402 by inserting a portion of the guide wire through entry slot 2406 of guide wire opening 2404 and into locking slot 2407. Locking slot 2407 frictionally secures the guide wire relative to body member 2402. Likewise, entry slot 2408 of catheter opening 2405 is dimensioned to be larger than the diameter of a catheter. Locking slot 2409 of catheter opening 2405 is dimensioned to be somewhat smaller than the diameter of a catheter. Accordingly, a catheter can be secured to body member 2402 by inserting a portion of the catheter through entry end 2408 of catheter opening 2405 and into locking slot 2409. Locking slot 2409 frictionally secures the catheter relative to body member 2402.

Figure 25:
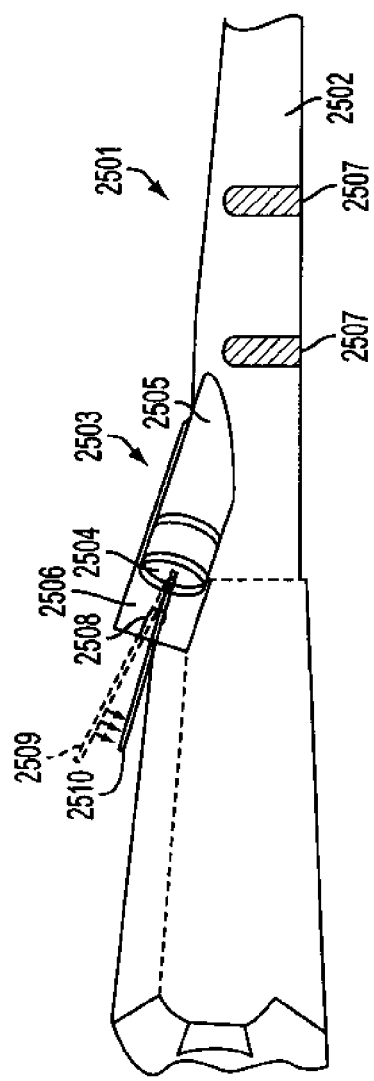
FIG. 25 is a partial side view of an illustrative locking device positioned on an endoscope having an angled side port.

FIG. 25 is a partial side view of an illustrative locking device positioned on an endoscope with an angled side port extending therefrom. The endoscope is generally shown at 2501, and includes main shaft 2502 with a lumen extending therethrough. Side port 2503 extends laterally away from main shaft 2502 at an angle. Side port 2503 provides access to the lumen of main shaft 2502. Accordingly, a guide wire and/or catheter may access the lumen of main shaft 2502 via side port 2503. Side port 2502 preferably includes side port opening 2504 which is laterally spaced from main shaft 2502 due to the angular displacement between main shaft 2502 and side port 2503. Side port opening 2504 is in fluid communication with the lumen of main shaft 2502 via connection tube 2505. Connection tube 2505 intersects a side wall of main shaft 2502 at an angle, as shown.

A locking device having body member 2506 is shown clipped onto main shaft 2502 of endoscope 2501. Body member 2506 includes a number of hook members 2507 for attaching the locking device to main shaft 2502. Two hook members are visible in FIG. 25. Hook members 2507 are similar to hook members 2403 described above with respect to FIG. 24. Body member 2506 extends away from hook members 2507 and generally parallel to side port 2503. In FIG. 25, body member 2506 is obscured by main shaft 2502 and side port 2503. Body member 2506 extends upward past side port opening 2504, wherein a securing mechanism is provided. Preferably, the securing mechanism is a J-shaped guide wire opening 2508. As seen in FIG. 25, although partially obscured by main shaft 2502 and side port 2503 of endoscope 2501, the attachment means comprising hook members 2507 is connected to the distal end of the body member 2506 and the securing means comprising the locking slot of the guidewire opening 2508 is connected to the proximal end of body member 2506 such that attachment means such as hook members 2507 are disposed distal of side port opening 2504 and securing are positioned proximal of side port opening 2504.

In use, a guide wire is advanced into the body via the endoscope. During the advancement of the guide wire, the proximal end thereof may be moved to first position 2509, which is in the entry slot of guide wire opening 2508. Once the guide wire is in a desired position within the body, the guide wire may be moved to second position 2510, which is in the locking slot of guide wire opening 2508. The locking slot of guide wire opening 2508 frictionally secures the guide wire relative to body member 2506.

Figure 26:
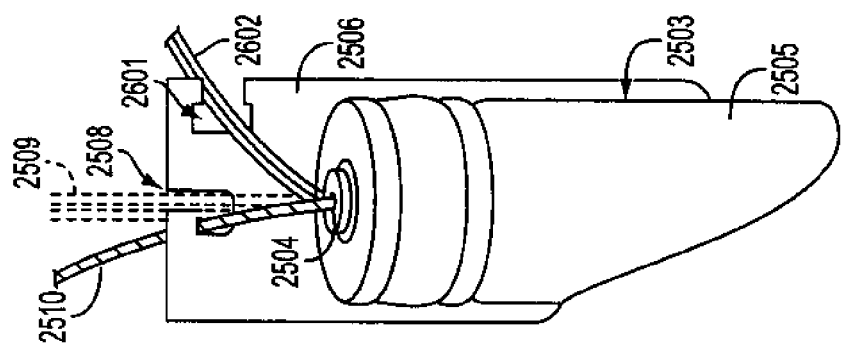
FIG. 26 is a partial side view detailing the illustrative locking device of FIG. 25.

FIG. 26 is a partial side view detailing the illustrative locking device of FIG. 25, with an additional oversized catheter opening shown. The side port of the endoscope is shown at 2503, and the body member of the locking device is shown at 2506. Positioned proximate side port opening 2504 is guide wire opening 2508 and oversized catheter opening 2601. Like above, the guide wire opening is J-shaped and includes an entry slot and a locking slot. Thus, the guide wire may be moved to first position 2509, which is in the entry slot of guide wire opening 2508. Once the guide wire is in a desired position within the body, the guide wire may be moved to second position 2510, which is in the locking slot of guide wire opening 2508. The locking slot of guide wire opening 2508 frictionally secures the guide wire relative to body member 2506.

Oversized catheter opening 2601 is sized to restrict lateral movement of catheter 2602 but not longitudinal movement of catheter 2602. Providing a guide wire opening that can secure the guide wire relative to body member 2506 and oversized catheter opening 2601 for only restricting lateral movement of catheter 2602 may be particularly useful in performing a catheter exchange procedure. For example, during a catheter exchange procedure, guide wire opening 2508 may maintain the position of the guide wire. The oversized catheter opening 2601 may separate the catheter from the guide wire, as the catheter is withdrawn. The first and second catheters should be single-operator exchange type catheters to provide access to the guide wire during the exchange.

FIG. 27 is a perspective view of another illustrative locking device. The embodiment shown in FIG. 27 is similar to the embodiment shown in FIG. 24, but the hook members are laterally offset rather than aligned. For example, hook member 2701 is laterally offset from hook member 2702 by a distance "D". This configuration is another example of an attachment mechanism for attaching the body member to a catheter shaft.

Figure 28:
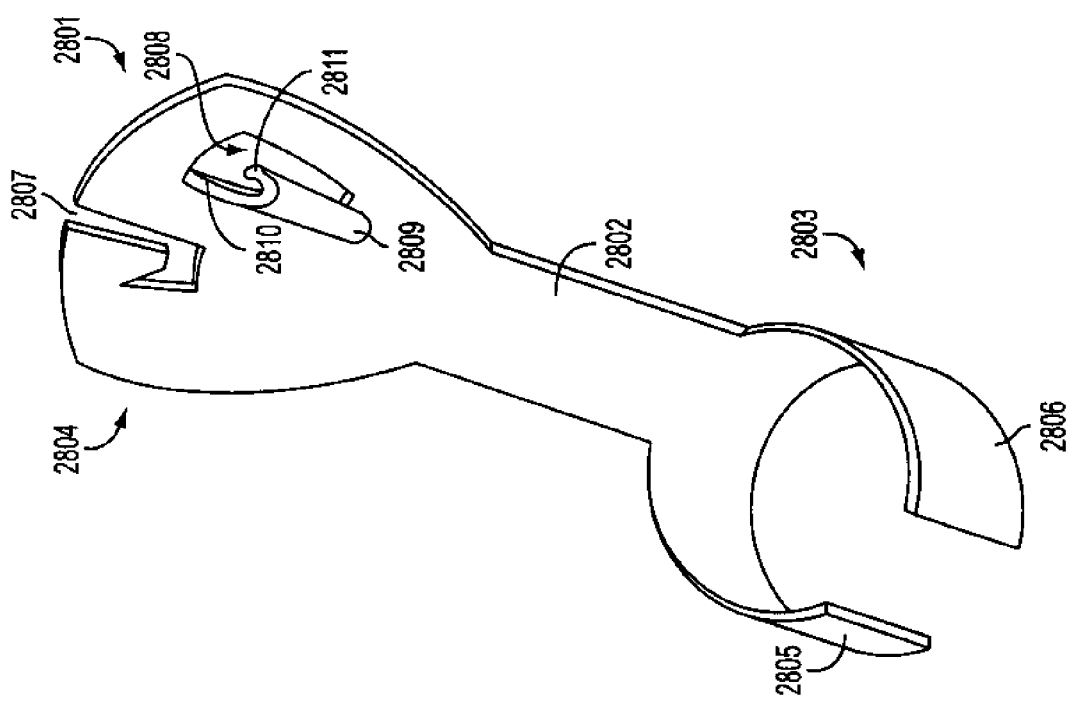
FIG. 28 is a perspective view of yet another illustrative locking device.

FIG. 28 is a perspective view of yet another illustrative locking device. The locking device is generally shown at 2801, and includes body member 2802 having attachment mechanism 2803 at one end and securing mechanism 2804 at the other. Attachment mechanism 2803 includes first hook member 2805 and second hook member 2806. First hook member 2805 and second hook member 2806 are adapted to extend around a substantial portion of the shaft of an endoscope or the like. Thus, first hook member 2805 and second hook member 2806 may clip body member 2802 to the desired shaft.

Securing mechanism 2804 includes i-shaped guide wire opening 2807 and flap-type catheter opening 2808. J-shaped guide wire opening 2807 operates similar to that described above. Flap-type catheter opening 2808 has flap 2809 formed by cutting catheter opening 2808 from body member 2802. Flap 2809 is preferably curved to form channel 2810, wherein end portion 2811 of channel 2810 loops back to near the surface of body member 2802. In this configuration, a catheter or guide wire may be selectively provided in channel 2810, which may bend flap 2809 away from body member 2802. Accordingly, flap 2809 may provide force between the guide wire or catheter and body member 2802 to effectively secure the guide wire or catheter to body member 2802.

Figure 29:
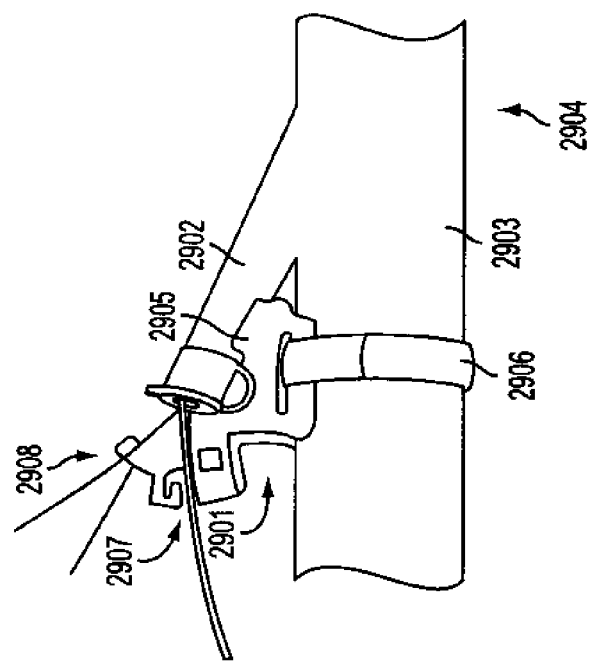
FIG. 29 is a partial side view of another illustrative locking device positioned on an endoscope having an angled side port.

FIG. 29 is a partial side view of yet another illustrative locking device 2901. Locking device 2901 is positioned between side port 2902 and main shaft 2903 of endoscope 2904. Locking device 2901 includes body member 2905 that is attached to main shaft 2903 using strap 2906. Preferably, strap 2906 extends around the entire circumference of main shaft 2903. Further, body member 2905 may include guide wire opening 2907 and one or more catheter openings 2908, as shown.

As previously described, the present invention relates to apparatus and methods used in positioning and maintaining the position of devices used in catheter procedures within the human anatomy. The present invention includes steerable devices, locking mechanisms and rapid exchange technologies to minimize or eliminate movement of endoscopic instruments during endoscopic procedures. Rapid exchange technologies may be included in the current invention to minimize movement of the devices when a guidewire is removed or a catheter is removed or exchanged.

Figure 30:
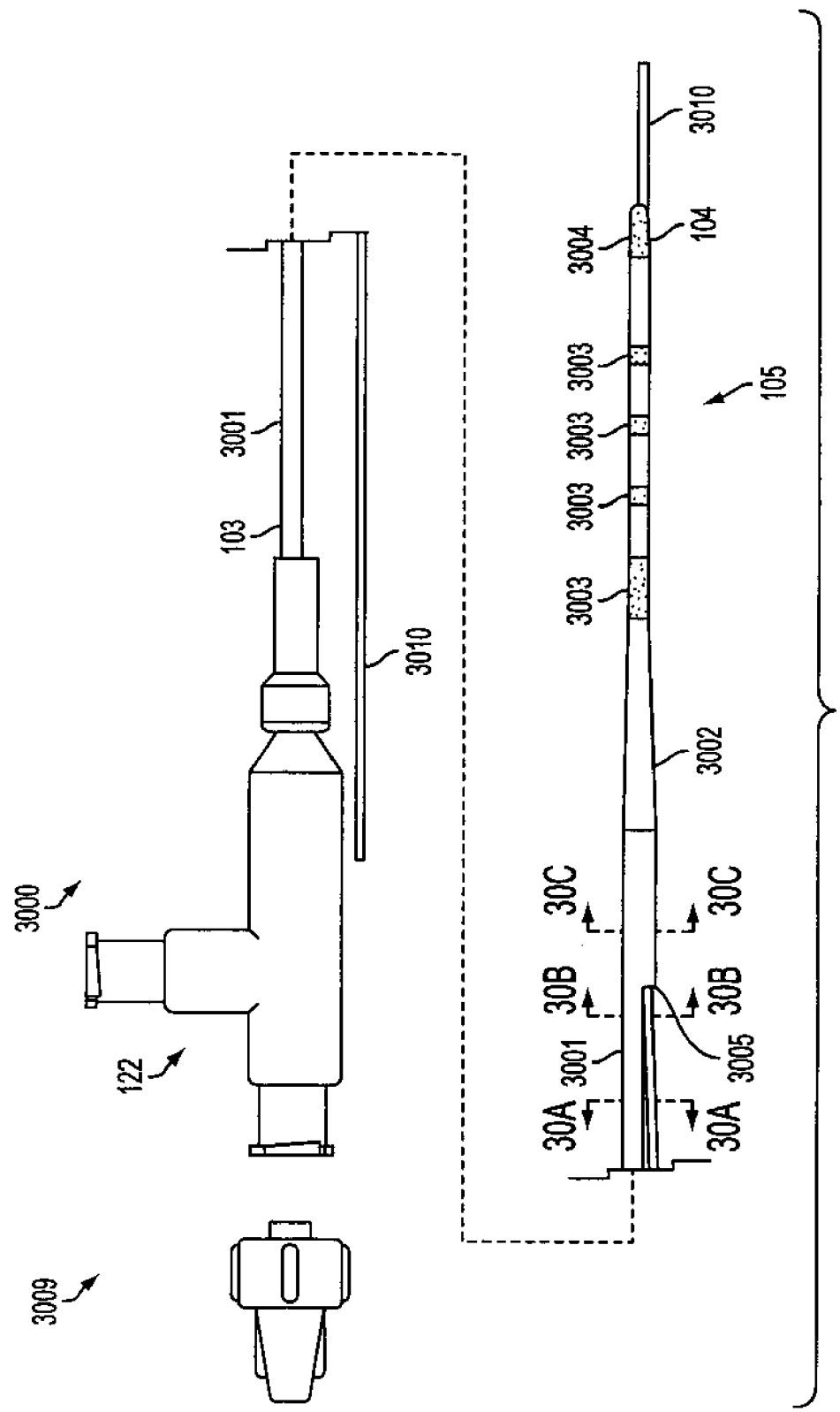
FIG. 30 is a partial elevational view of a catheter in accordance with the present invention having a guidewire lumen for facilitating rapid catheter exchange with a guidewire passing therethrough.

FIG. 30 shows a partial elevational view of catheter assembly 3009 in accordance with the present invention. Catheter assembly 3009 is used in catheter procedures for accessing targeted anatomical regions through the alimentary canal. The present invention incorporates features which allow rapid exchange of catheter by a single operator. The catheter of the present invention allows shorter length guidewires to be used, resulting in procedures which require less medical personnel, are less time consuming, and less costly. Additionally, the present invention is adaptable to most catheter devices used for catheter procedures within the alimentary canal.

Catheter assembly 3009 includes catheter 3000 having guidewire 3010 passing through a portion thereof. Catheter 3000 includes shaft 3001 having proximal end 103 and distal end 104. Operably connected to proximal end 103 of shaft 3001 is catheter hub assembly 122. Catheter hub assembly 122 couples to ancillary devices allowing access to a lumen within shaft 3001. Shaft 3001 is preferably formed in an extrusion process. Shaft 3001 may be formed of an extruded polymeric material. In one embodiment, the preferred polymeric material is polytetrafluoroethylene, polyether block amide, nylon or a combination or blend of these. Catheters which are contemplated include, but are not limited to, cannulas, sphincterotomes, cytology devices, and devices for stone retrieval and stent placement.

Shaft 3001 is a generally tubular shaped member having a generally uniform outer shape at its proximal end. Shaft 3001 may be sized for slidable passage through the lumen of an endoscope. Shaft 3001 includes distal taper 3002 which tapers to distal portion 105. Distal portion 105 may include high contrast, color coded distal markers 3003, and radiopaque distal tip 3004 for fluoroscopic visualization of distal portion 105 during a catheter procedure.

Figure 30A:
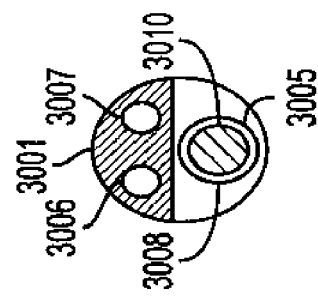
FIG. 30A is a cross-sectional view of the catheter of FIG. 30 taken along line 30A-30A.

Shaft 3001 further includes proximal port or opening 3005 located proximal of distal end 104. Proximal opening 3005 allows access to shaft 3001 for passage of guidewire 3010 through shaft 3001. FIG. 30A is a cross-sectional view of shaft 3001 taken along line 30A-30A at a location proximal of proximal opening 3005. Proximal to proximal opening 3005, guidewire 3010 is positioned adjacent catheter shaft 3001.

Extending longitudinally between the shaft proximal end 103 and distal end 104 is an ancillary lumen 3006 and a second ancillary lumen 3007. Ancillary lumen 3006 and ancillary lumen 3007 may be injection lumens, allowing for high contrast media flow capability for bubble-free opacification and for excellent visualization of a desired anatomical region. Additionally or alternatively, ancillary lumen 3006 and/or ancillary lumen 3007 may be used for other ancillary devices, such as a cutting wire lumen or a retrieval balloon lumen.

Figure 30B:
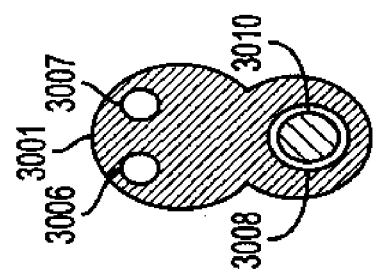
FIG. 30B is a cross-sectional view of the catheter of FIG. 30 taken along line 30B-30B.
Figure 30C:
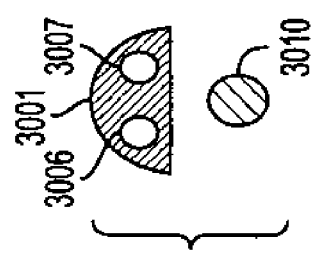
FIG. 30C is a cross-sectional view of the catheter of FIG. 30 taken along line 30C-30C.

Referring to FIG. 30B, a cross-sectional view of shaft 3001 taken along line 30B-30B of FIG. 30 is shown. Guidewire lumen 3008 extends between proximal opening 3005 and distal end 104. Guidewire 3010 may enter guidewire lumen 3008 at proximal opening 3005. Guidewire lumen 3008 is sized for slidable receipt and passage of guidewire 3010 through guidewire lumen 3008. Referring to FIG. 30C, guidewire lumen 3008 extends through distal taper 3002 and distal portion 105. Guidewire lumen 3008 may also extend from distal end guidewire 104.

Although it is recognized that proximal opening 3005 may be located at any location distal of proximal end 103, proximal opening 3005 is preferably located less than 25 cm from distal end 104. Guidewire lumen 3008 is a tubular member which is carried adjacent shaft 3001 ancillary lumen 3006 and ancillary lumen 3007. Guidewire lumen 3008 may be formed integral with shaft 3001, or alternatively, guidewire lumen

Figure 30D:
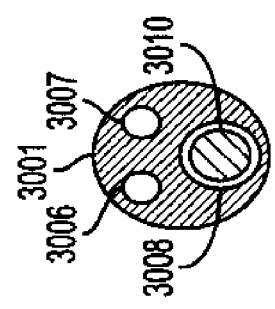
FIG. 30D is a cross-sectional view of an alternative embodiment of the catheter of FIG. 30 in accordance with the present invention, also taken along line 30C-30C.

3008 may be part of a separate tubular member which is coupled to shaft 3001 as shown in FIG. 30D.

Figure 30E:
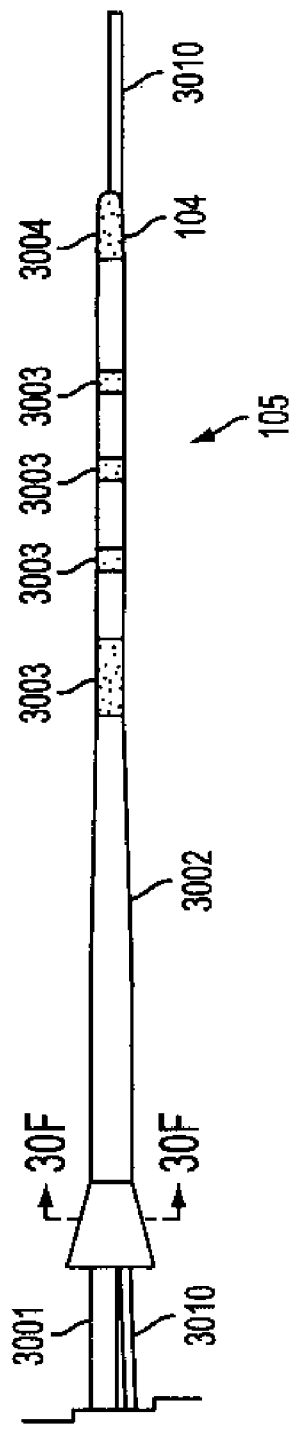
FIG. 30E is a partial elevational view of an alternative embodiment of the catheter in accordance with the present invention.
Figure 30F:
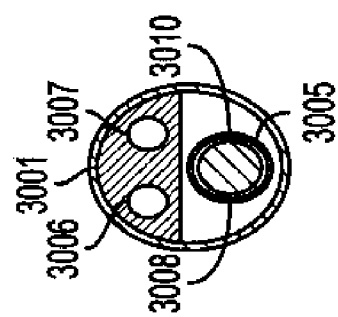
FIG. 30F is a cross-sectional view of the catheter of FIG. 30E taken along line 30E-30F.

Now referring to FIGS. 30E and 30F, an alternative embodiment of the catheter depicted in FIG. 30 is illustrated. Catheter shaft 3001 of FIG. 30E incorporates a proximal guidewire opening which, in conjunction with the catheter, forms a circular cross section which allows for easy insertion of the guidewire. As depicted in FIG. 30F, guidewire lumen 3008 can include a larger proximal opening which funnels down to the size of guidewire lumen 3008 which extends distal to the distal end of catheter shaft 3001.

Guidewire lumen 3008 allows rapid exchange of catheter 3000 when an alternative catheter is necessary during a procedure. Shorter length guidewires may be used since guidewire 3010 does not pass through proximal end 103 and catheter hub assembly 122, but rather enters catheter shaft 3001 at proximal opening 3005 located substantially distal from proximal end 103. The unique catheter construction in accordance with the present invention will reduce catheter therapeutic and diagnostic procedure time since catheter device exchanges may be performed relatively more easily and quickly by a single operator. Additional personnel and time associated with maintaining the placement of a conventional (approximately 400 cm) guidewire within the targeted anatomical region is eliminated, reducing the overall costs of the procedure.

Figure 31:
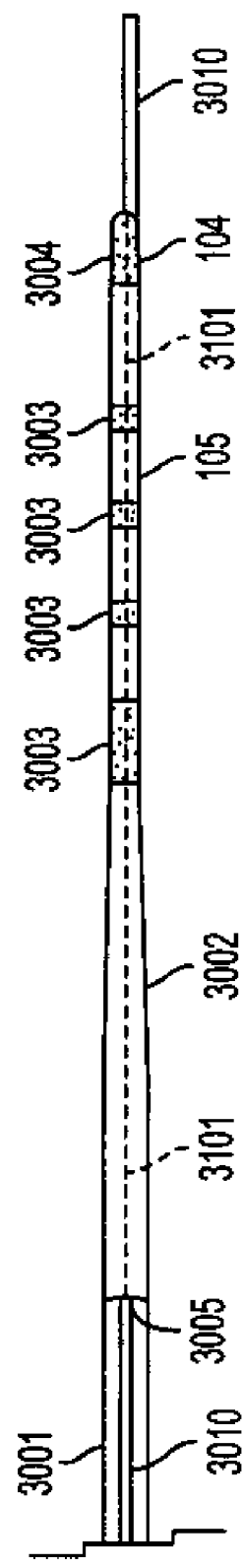
FIG. 31 is a partial elevational view of another embodiment of the catheter in accordance with the present invention.

Referring to FIG. 31, a partial elevational view of a distal portion of catheter shaft 3001 is shown. Shaft 3001 may further include weakened area 3101. Weakened area 3101 extends longitudinally along guidewire lumen 3008 (not shown) between proximal opening 3005 and distal end 104.

When guidewire 3010 is positioned within guidewire lumen 3008, weakened area 3101 allows guidewire 3010 to be removed from guidewire lumen 3008 by "peeling away" guidewire 3010 from catheter shaft 3001. Weakened area 3101 may include less catheter material than the remaining portion of catheter shaft 3001, or may be perforated, cut or slit.

At least two different embodiments of weakened area 3101 are possible. In a first embodiment, weakened area 3101 is formed, and a slit, perforation or cut is introduced along the length of weakened area 3101 on the outside of catheter 3002 along the side of catheter 3002 which contains guidewire lumen 3008. In this embodiment, when removal of catheter 3002 is desired, a "directed tear" is performed in which the tear in guidewire lumen 3008 (and catheter 3002) follow the slit, cut or perforation. In a second embodiment, weakened area 3101 is formed by extruding catheter 3002 in a manner which creates sidewalls of catheter 3002 thin enough to be torn without requiring slits, cuts or perforations to be introduced after the catheter is extruded. In this embodiment, when catheter 3002 is to be removed, a non-directional tear occurs in the outside wall of guidewire lumen 3008. One of ordinary skill in the art would appreciate that the thin wall approach would reduce manufacturing costs and ensure catheters are single use items. The thin wall configuration may also be configured after extrusion such as by stretching the catheter, molding, or similar procedures.

Another embodiment of the present invention is shown generally in FIG. 32. FIG. 32 is a partial elevational view of catheter 3000, which may be a "convertible" catheter design. In catheter 3000, shaft 3001 includes opening 3005 which is skive port 3201 for access to guidewire lumen 3008. Catheter 3000 is a convertible catheter design in that an existing catheter may be modified to include skive port 3201. As a convertible catheter design, skive port 3201 is formed by cutting an opening in shaft 3001 for access to guidewire lumen 3008. It is recognized that catheter 3000 may be manufactured to include skive port 3201.

Referring to FIG. 32A, proximal to skive port 3201 catheter shaft 3001 includes ancillary lumen 3006 and ancillary lumen 3007 as previously described herein. Additionally, shaft 3001 includes guidewire lumen 3008 extending between proximal end 103 and distal end 104, including between skive port 3201 and proximal end 103. Referring to FIG. 32B, guidewire 3010 may access guidewire lumen 3008 at skive port 3201 and extend through guidewire lumen 3008, emerging from distal end 104.

With this embodiment, conventional guidewire techniques may be used for positioning and exchanging catheter 3000 within a patient's alimentary canal system. Further, the convertible catheter design incorporates features which allow rapid exchange of catheters by a single operator. Skive port 3201 opening 3005 allows catheter 3000 to be used in rapid exchange of catheter 3000 when an alternative catheter is necessary during a procedure. By allowing guidewire 3010 to enter guidewire lumen 3008 a location distal from proximal end 103, relatively shorter guidewires may be used during catheter procedures within the alimentary canal system, resulting in a more efficient and less costly procedure.

It is recognized that other means for accessing guidewire lumen 3008 at a location distal from proximal end 103 are contemplated within the scope of the present invention. Referring to FIG. 33, a weakened location or slit 3301 is shown within area A for accessing guidewire lumen 3008. Referring to FIG. 33A, proximal to slit 3301, guidewire 3010 may be positioned adjacent catheter shaft 3001. Guidewire 3010 enters guidewire lumen 3008 at slit 3301 for passage of guidewire 3010 through guidewire lumen 3008. Referring to FIG. 33B, guidewire 3010 is slidably contained within guidewire lumen 3008 at a location distal of slit 3301. With this embodiment, since guidewire lumen 3008 may extend longitudinally from proximal end 103 to distal end 104, conventional guidewire techniques may also be used during the catheter procedure.

Figure 34:
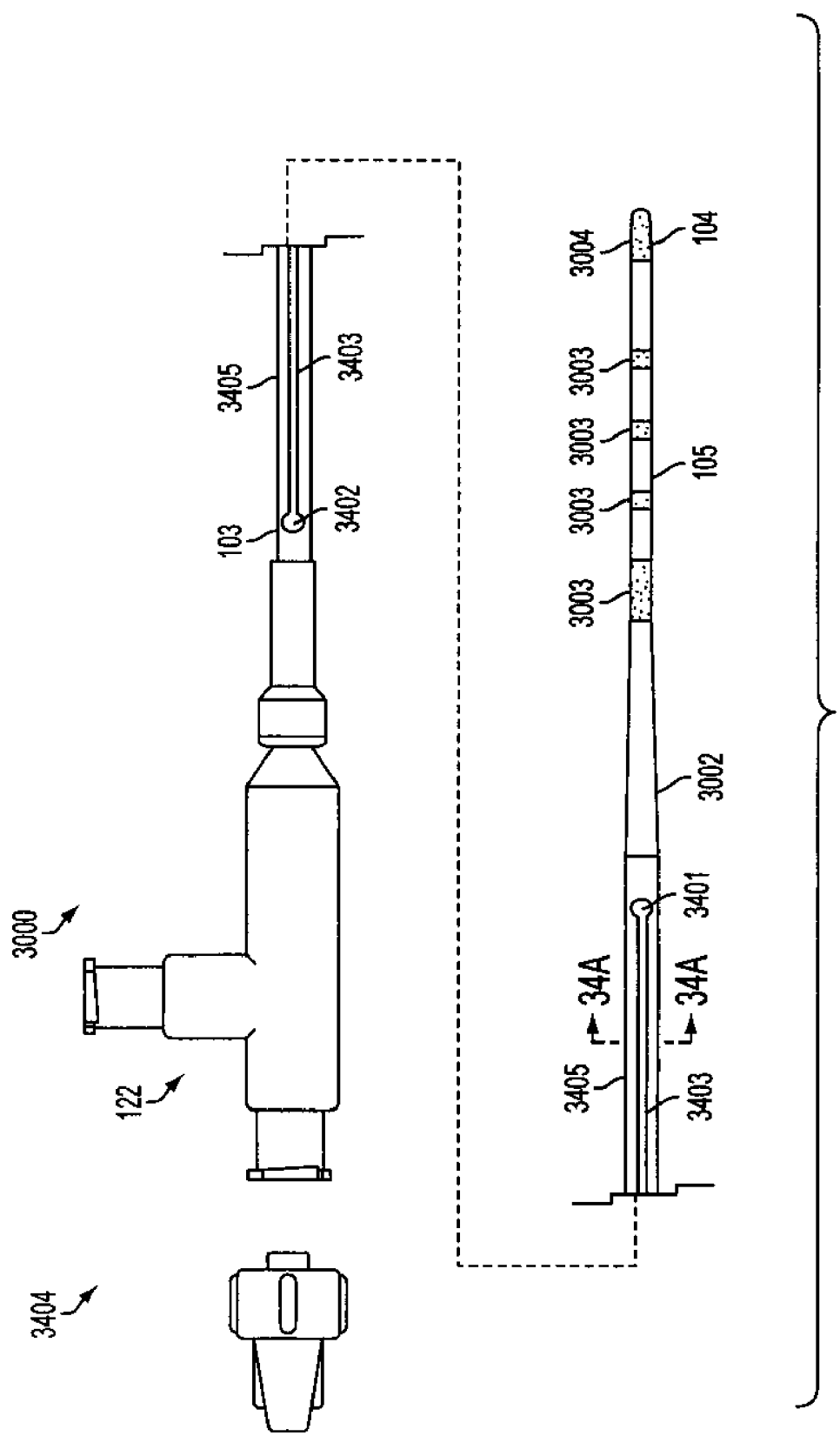
FIG. 34 is a partial elevational view of another embodiment of the catheter in accordance with the present invention.

Referring to FIG. 34, another embodiment of the catheter of the present invention incorporating features which allow rapid exchange of catheters by a single operator is generally shown. Catheter assembly 3004 includes a "port and channel" configuration. For access to guidewire lumen 3008, shaft 3005 includes a first opening or intermediate port 3401 located proximal of distal end 104. A second opening or proximal port 3402 is located proximal of intermediate port 3401 and proximal of distal end 104. Extending between intermediate port 3401 and proximal port 3402 is longitudinal channel 3403.

Figure 34A:
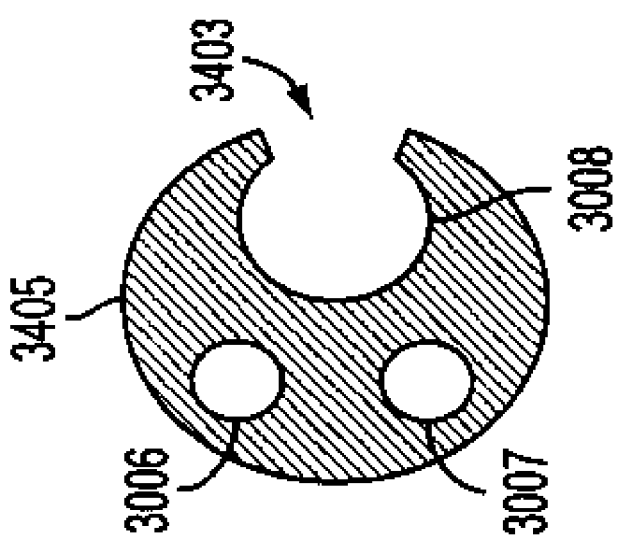
FIG. 34A is a cross-sectional view of the catheter of FIG. 34 taken along line 34A-34A.

Guidewire lumen 3008 extends longitudinally between proximal end 103 and distal end 104. Referring to FIG. 34A, channel 3403 is located within the wall of catheter shaft 3405, providing access to guidewire lumen 3008 between proximal port 3402 and intermediate port 3401. Preferably, channel 3403 includes a radial opening extending between proximal port 3402 and intermediate port 3401. It is also recognized that channel 3403 may be a weakened area within the wall of the catheter shaft, a perforated area, or a slit which extends between proximal port 3402 and intermediate port 3401. Channel 3403 may also be included by manufacturing catheter 3405 with thinner exterior walls.

Figure 35A:
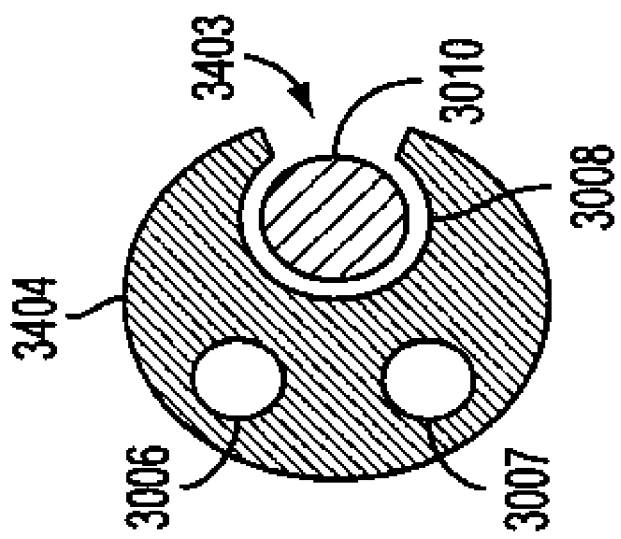
FIG. 35A is a cross-sectional view of the catheter of FIG. 35 taken along line 35A-35A showing the guidewire received within the lumen of FIG. 34.
Figure 35:
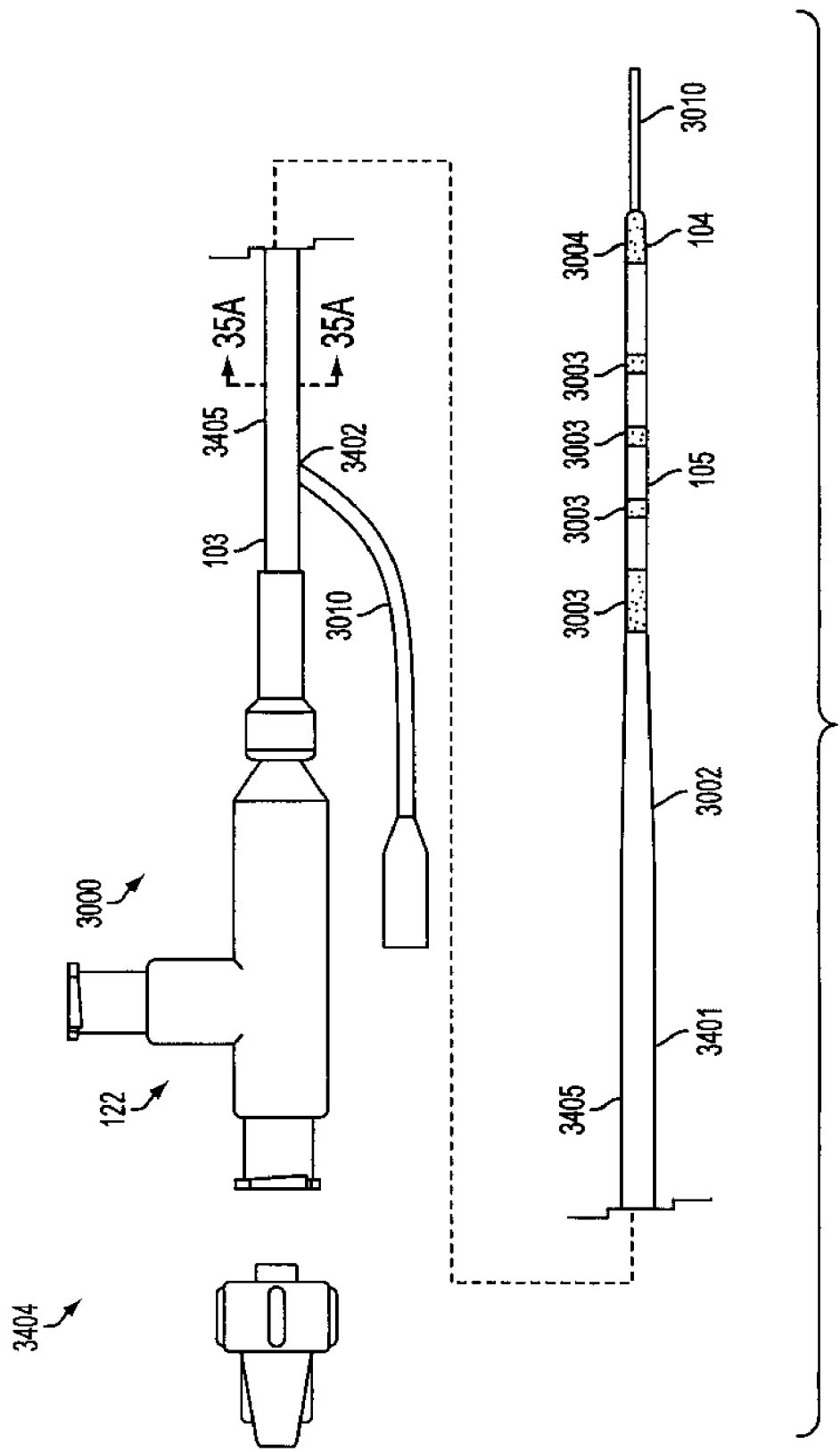
FIG. 35 is a different partial elevational view of the catheter of FIG. 34 having a guidewire disposed therein.

In one embodiment, intermediate port 3401 is located near distal end 104, and proximal port 3402 is located near proximal end 103. Referring to FIG. 35, distal end 104 of guidewire 3010 may be inserted within intermediate port 3401 (not shown), passing through guidewire lumen 3008, and emerging from catheter 3000 distal end 104. Referring also to FIG. 35A, guidewire 3010 may then be snapped through channel 3403 into guidewire lumen 3008 with the proximal end of guidewire 3010 exiting proximal port 3402. With this "port and channel" design, both conventional and rapid exchange techniques may be used.

Figure 36:
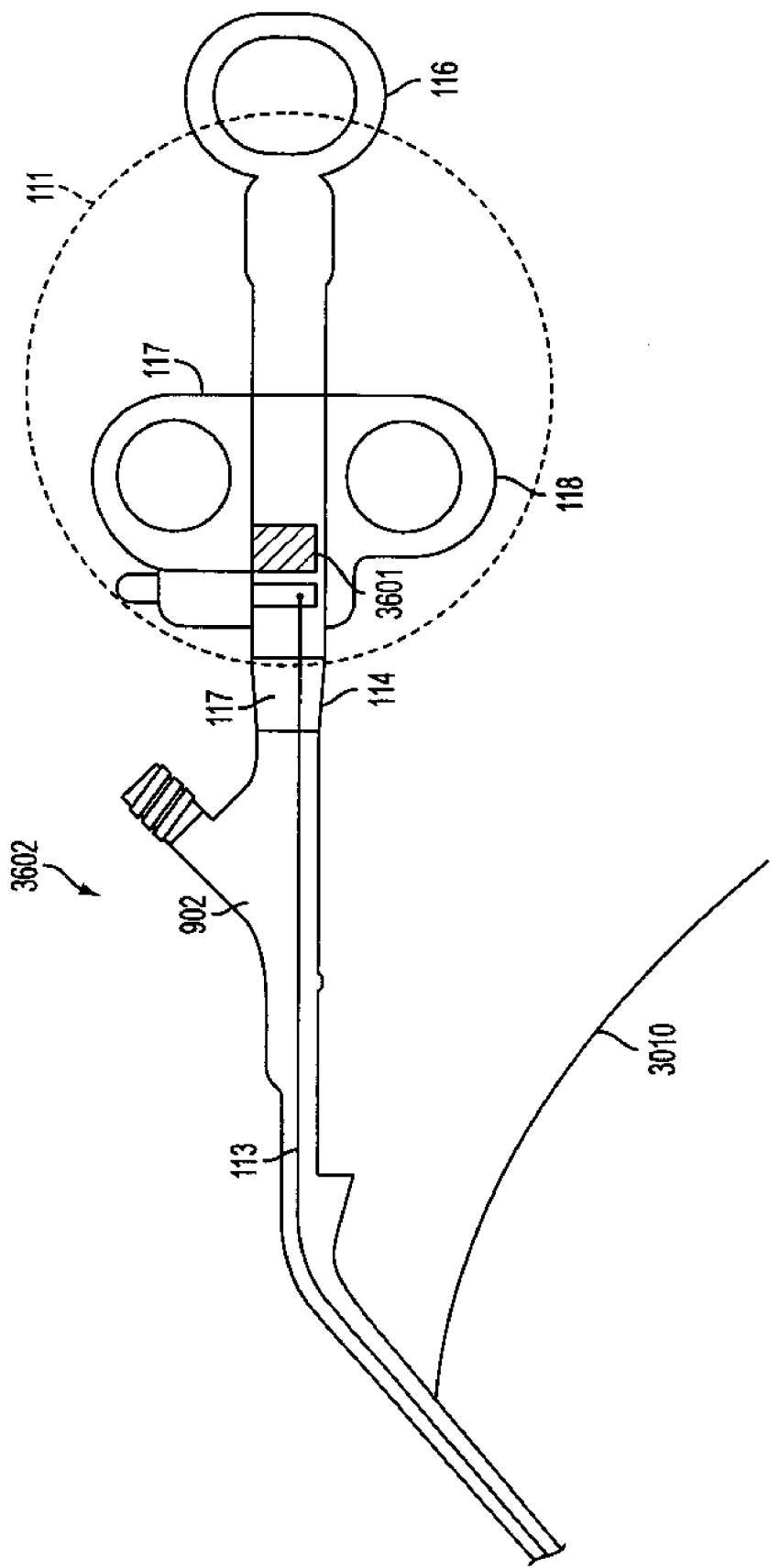
FIG. 36 shows a cut away diagram of an embodiment of the current invention which incorporates the rotating handle, locking mechanism and rapid exchange technology into a single catheter.

FIG. 36 shows a cut away diagram of an embodiment of the current invention which incorporates the rotating handle 111, locking mechanism 3601 and rapid exchange technology into catheter 3602. In FIG. 36, cutting wire 113 is attached to handle 111 as described with respect to FIGS. 8 and 8A. As handle 111 is rotated, distal end (not shown) of cutting wire 113 is also rotated to position a cutting portion (not shown) of cutting wire 113 in a desired orientation. Clicks or other audible indications may also be incorporated into catheter 3602 to indicate an amount of rotation accepted by handle 111 to an operator. A rotation lock as described in FIGS. 10-14D may also be incorporated into catheter 3602. The outside of bifurcation connector and body section 117 may also include a rotation marker. Guidewire 3010 may enter guidewire lumen 3008 through a proximal port or opening, as described with respect to FIGS. 30-33B, or through a skive port as described in FIGS. 34-35A. Guidewire 3010 may be removed from catheter 3601 through a slit, perforation, cut, or thinned wall of catheter 3602 as described with respect to FIGS. 30-31. This procedure may permit the placement of a second catheter over the proximal end of a guidewire and proximal to the first catheter to allow rapid introduction of the second catheter once the first catheter is torn away.

Figure 37:
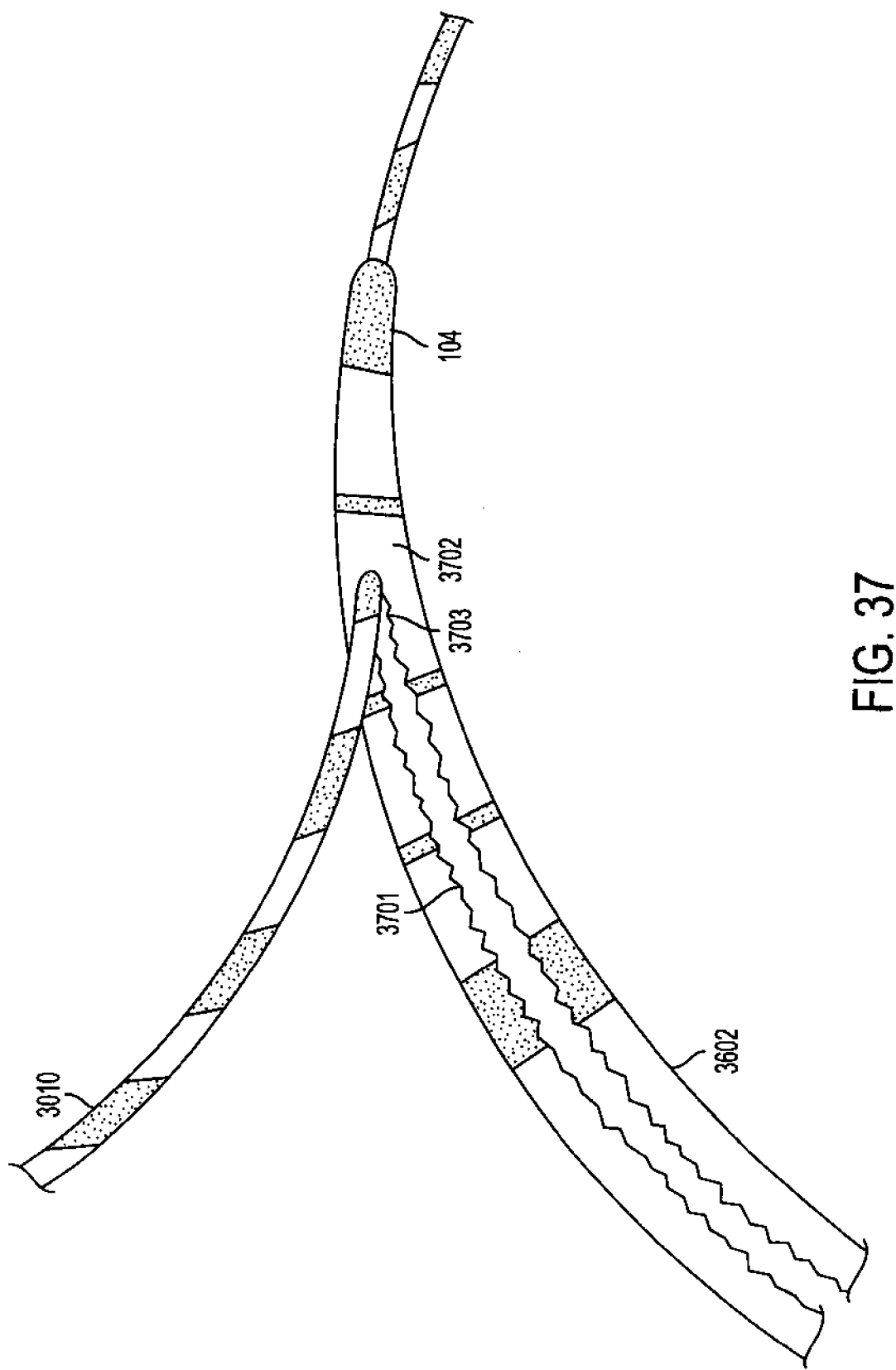
FIG. 37 shows a non-directional tear in a thinned-wall catheter.

FIG. 37 shows a non-directional tear in a thinned-wall catheter 3602. When it is desired to separate catheter 3602 from guidewire 3010, a force is exerted on guidewire 3010 in a direction away from catheter 3602, or on catheter 3602 in a direction away from guidewire 3010 which causes catheter 3602 to tear 3701 in a non-directional manner. One of ordinary skill in the art would appreciate from FIG. 37 that catheter 3602 above point 3703 where guidewire 3010 contacts catheter 3602 has not been perforated, cut or slit as indicated near reference number 3702. As additional pressure is exerted on guidewire 3010 or catheter 3602, tear 3701 will continue toward distal end 104.

FIG. 38 shows catheter 3602 positioned through endoscope 3801 detailing the relationship of the guidewire and the catheter when a rapid exchange catheter is used. When a catheter exchange is required or desired, the position of guidewire 3010 may be maintained by withdrawing catheter 3602 from the patient and tearing catheter 3602 from guidewire 3010.

FIG. 38A is a sectional view along line 38A-38A of FIG. 38. As catheter 3801 is torn from guidewire 3010, a portion of the thinned wall of catheter 3801 is torn in a non-directional manner 3802. One of ordinary skill in the art would appreciate that by introducing slits, cuts or perforations into catheter 3801, a directional tear may be assured.

While the present invention is described in terms of a catheter used in accessing the biliary tree, one of ordinary skill in the art would appreciate that the present invention includes the introduction of an endoscopic instrument into any body lumen. In other embodiments, the present invention may be used to position and maintain the orientation of an endoscopic instrument within any body lumen. For example, the present invention may be incorporated into a catheter for use in, but not limited to, the pulmonary system, vascular ducts, or urino-genital procedures.

What is claimed is:

1. An apparatus for the accurate positioning of endoscopic instruments, comprising:
an elongate catheter shaft having a proximal portion, a distal portion, an outer surface, and a lumen formed therein;
a handle coupled to the proximal portion of the catheter shaft;
a cutting wire having a first portion attached to the distal portion of the catheter shaft, a second portion disposed along the outer surface of the catheter shaft, and a third portion attached to the handle;
wherein the handle is coupled to the catheter shaft with a rotatable coupling that allows the handle to rotate independently of the catheter shaft;
a rotation indicator that is configured to indicate the amount of rotation of the handle relative to the catheter shaft; and
wherein the rotation indicator includes an audible indicator.

2. The apparatus of claim 1, further comprising a locking mechanism for locking the position of the first portion of the cutting wire.

3. The apparatus of claim 1, wherein the rotation indicator includes a visual indicator.

4. The apparatus of claim 1, wherein the distal portion of the catheter shaft has a first outer diameter and wherein the proximal portion of the catheter shaft has a second outer diameter greater than the first outer diameter.

5. The apparatus of claim 1, wherein the catheter shaft has two or more lumens formed therein.

6. The apparatus of claim 5, wherein the catheter shaft has three lumens formed therein.

7. A medical device, comprising:
an elongate catheter shaft having a proximal portion, a distal portion, an outer surface, and a lumen formed therein;
a handle coupled to the proximal portion of the catheter shaft;
a cutting wire having a first portion attached to the distal portion of the catheter shaft, a second portion disposed along the outer surface of the catheter shaft, and a third portion extending through the lumen and being attached to the handle;
wherein the handle is coupled to the catheter shaft with a rotatable coupling that allows the handle and the cutting wire to rotate independently of the catheter shaft; and
a rotation lock for preventing rotation of the catheter shaft relative to the handle, the rotation lock being disposed between the handle and the shaft and allowing for the handle to be released from the catheter shaft.

8. The medical device of claim 7, further comprising a rotation indicator that is configured to indicate the amount of rotation of the handle relative to the catheter shaft.

9. The medical device of claim 7, wherein the rotation lock includes a first pair of detents and the handle includes a second pair of detents configured to mate with the first pair of detents.

10. The medical device of claim 7, wherein the rotation lock is a friction lock that includes a post that frictionally engages the handle.

11. The medical device of claim 10, wherein the post includes an oval post.

12. The medical device of claim 10, wherein the post includes a triangular post.

13. The medical device of claim 10, wherein the post includes a square post.

14. The medical device of claim 7, wherein the handle includes a brake configured to resist movement of a guidewire within the catheter shaft.

15. A medical device, comprising:
an elongate catheter shaft having a proximal portion, a distal portion, an outer surface, and a lumen formed therein;
a handle coupled to the proximal portion of the catheter shaft, the handle being rotatable relative to the catheter shaft;
a cutting wire having a first portion attached to the distal portion of the catheter shaft, a second portion disposed along the outer surface of the catheter shaft, and a third portion extending through the lumen and being attached to the handle;
a rotation lock for preventing rotation of the catheter shaft relative to the handle; and
wherein the rotation lock is disposed between the handle and the shaft and allows for the handle to be released from the catheter shaft.

16. A medical device, comprising:
an elongate catheter shaft having a proximal portion, a distal portion, an outer surface, and a lumen formed therein;
a handle coupled to the proximal portion of the catheter shaft, the handle being rotatable relative to the catheter shaft;
a cutting wire having a first portion attached to the distal portion of the catheter shaft, a second portion disposed along the outer surface of the catheter shaft, and a third portion extending through the lumen and being attached to the handle;
a rotation lock disposed between the handle and the catheter shaft for preventing rotation of the catheter shaft relative to the handle; and
wherein the rotation lock is a friction lock that includes a post that frictionally engages the handle.

17. A medical device, comprising:
an elongate catheter shaft having a proximal portion, a distal portion, an outer surface, and a lumen formed therein;
a handle coupled to the proximal portion of the catheter shaft, the handle being rotatable relative to the catheter shaft;
a cutting wire having a first portion attached to the distal portion of the catheter shaft, a second portion disposed along the outer surface of the catheter shaft, and a third portion extending through the lumen and being attached to the handle;
a rotation lock for preventing rotation of the catheter shaft relative to the handle; and
a guidewire extending through the catheter shaft;
wherein the handle includes a brake that is configured to resist movement of the guidewire relative to the catheter shaft.

* * * * *

UNITED STATES PATENT AND TRADEMARK OFFICE
CERTIFICATE OF CORRECTION

| | | |
|---|---|---|
| PATENT NO. | : 8,231,621 B2 | Page 1 of 1 |
| APPLICATION NO. | : 12/639709 | |
| DATED | : July 31, 2012 | |
| INVENTOR(S) | : John E. Hutchins et al. | |

It is certified that error appears in the above-identified patent and that said Letters Patent is hereby corrected as shown below:

In the Specifications

Column 7
Line 53: delete "30E" and insert therefor -- 30F --.

Column 7
Line 61: delete "3213" and insert therefor -- 32B --.

Column 15
Line 48: after "to" and before "locking", delete "to".

Column 17
Line 36: delete "i-shaped" and insert therefor -- J-shaped --.

Signed and Sealed this
Eighth Day of January, 2013

David J. Kappos
*Director of the United States Patent and Trademark Office*